United States Patent [19]

Stobart et al.

[11] Patent Number: 4,950,798
[45] Date of Patent: Aug. 21, 1990

[54] PROCESS FOR CATALYTIC HYDROFORMYLATION

[75] Inventors: Stephen R. Stobart; Stephen L. Grundy; Frederick L. Joslin, all of Victoria, Canada

[73] Assignee: University of Victoria, Victoria, Canada

[21] Appl. No.: 284,366

[22] Filed: Dec. 14, 1988

[30] Foreign Application Priority Data

Jun. 29, 1988 [CA] Canada ............................ 570803

[51] Int. Cl.$^5$ ............................................. C07C 45/30
[52] U.S. Cl. ..................................... 568/454; 502/155; 502/165; 556/16; 556/9; 568/8; 568/451
[58] Field of Search ............... 568/454, 451; 556/8, 9; 502/155, 166; 454/10, 451

[56] References Cited

U.S. PATENT DOCUMENTS

| | | | |
|---|---|---|---|
| 3,239,566 | 3/1966 | Slaugh et al. | 568/454 |
| 3,278,612 | 10/1966 | Greene | 568/454 |
| 3,310,576 | 3/1967 | Mertzweiller et al. | 568/454 |
| 3,515,757 | 6/1970 | Sibert | 568/454 |
| 3,576,881 | 4/1971 | Senn . | |
| 3,917,661 | 11/1975 | Fruett et al. | 568/454 |
| 3,937,742 | 2/1976 | Yoo | 568/454 |
| 3,954,877 | 5/1976 | Gipson | 568/454 |
| 3,965,192 | 6/1976 | Booth | 568/454 |
| 3,976,596 | 8/1976 | Hawthorne et al. | 252/431 |
| 4,041,082 | 8/1977 | Onoda et al. | 568/454 |
| 4,052,461 | 10/1977 | Tinker et al. | 568/454 |
| 4,089,727 | 5/1978 | McLain | 156/356 |
| 4,089,881 | 5/1978 | Lukehart | 260/429 R |
| 4,108,905 | 8/1978 | Wilkinson | 568/454 |
| 4,139,565 | 2/1979 | Unruh et al. | 568/454 |
| 4,155,939 | 5/1979 | Poist | 568/454 |
| 4,169,861 | 10/1979 | Hughes | 568/454 |
| 4,200,592 | 4/1980 | Hignett et al. | 568/454 |
| 4,201,714 | 5/1980 | Hughes | 260/340.9 |
| 4,201,728 | 5/1980 | Hughes | 568/454 |
| 4,258,215 | 3/1981 | Dawes | 568/454 |
| 4,291,196 | 9/1981 | Spaniol et al. | 178/3 |
| 4,292,196 | 9/1981 | Homeier et al. | 251/412 |
| 4,298,541 | 11/1981 | Oswald et al. | 260/429 R |
| 4,358,621 | 11/1982 | Sakakibara et al. | 568/454 |
| 4,386,013 | 5/1983 | Callahan et al. | 252/431 P |
| 4,399,312 | 8/1983 | Russell et al. | 568/454 |
| 4,400,548 | 8/1983 | Abatjoglou et al. | 568/454 |
| 4,450,299 | 5/1984 | Oswald et al. | 568/454 |
| 4,451,673 | 5/1984 | Oswald et al. | 568/454 |
| 4,454,353 | 6/1984 | Oswald et al. | 568/454 |
| 4,480,137 | 10/1984 | Oswald et al. | 568/454 |

FOREIGN PATENT DOCUMENTS

| | | | |
|---|---|---|---|
| 729213 | 3/1966 | Canada | 568/454 |
| 820341 | 8/1966 | Canada | 568/454 |
| 905988 | 7/1972 | Canada | 568/454 |
| 951738 | 7/1974 | Canada | 568/454 |
| 1022934 | 12/1977 | Canada | 568/454 |
| 1082722 | 7/1980 | Canada | 568/454 |
| 1123859 | 5/1982 | Canada | 568/454 |
| 1191864 | 8/1985 | Canada | 568/454 |

OTHER PUBLICATIONS

Hendriksen et al, "Selective Rhodium-Catalyzed Hydroformylation with the Tri- and Tetraphosphine Ligands (CH$_3$) Si(CH$_2$CH$_2$PPh$_2$)$_3$, Formation of Rh[Si(CH$_2$CH$_2$PPh$_2$)$_3$](CO) via CH$_3$Si Bond Cleavage and Structure of This Rh(I)-Si Bonded Complex", Organometallics 1989, 8, 1153–1157.

Holmes-Smith et al, "Phosphinoalkylsilanes: Synthesis and Spectroscopic Properties of Phosphino(silyl)methanes, 1-Phosphino-2-silylethanes, and 1-Phosphine-3-silylpropanes", J. Chem. Soc. Perkin Trnas. I, 1983, 861–866.

Auburn et al, (Phosphinoalkyl)silyl Complexes, 3.[1] "Chelate-Assisted" Hydrosilylation: Formation of Enantiomeric and Diastereoisomeric Iridium(III) Complexes with Chelating (Phosphinoethyl)silyl Ligands, Journal of the American Chemical Society, 1984, vol. 106, No. 5, 1314.

Auburn et al, "Intramolecular Rearrangement Behaviour of a Dihydridoiridium(iii) Complex Formed by regiospecific 'Chelate-Assisted' Hydrosilylation", J. Chem. Soc., Chem. Commun., 1984, 281–282.

Auburn et al, "Phosphinoalkylsilyl Complexes, 6.[1] Isolation of a Silyl Complex of Iridium(I), Crystal and Molecular Structure of Dicarbonyl(triphenylphosphine)-[((diphenylphosphino)ethyl)dimethylsilyl] iridium", J. Am. Chem. Soc. 1985, 107, 266–267.

Auburn et al, "Phosphinoalkyllsilyl Compleses, 5.[1] Synthesis and Reactivity of Congeneric Chelate-Stabilized Disilyl Complexes of Rh(III) and Ir(III): Chlorobis[Diphenylphosphinoethyl(Dimethyl)Silyl]-Rhodium and -Iridium", Inorg. Chem. 24, 318–323, 1985.

Primary Examiner—Werren B. Lone
Attorney, Agent, or Firm—Nixon & Vanderhye

[57] ABSTRACT

A novel hydroformylation process for the conversion of olefins having up to about 20 carbon atoms to their corresponding aldehydes is provided herein involving the use of catalysts comprising chelates in which a ligand is chelated at a metal center to produce at least one heterocyclic ring with the central metal atom as part of the ring, i.e., platinum-group metal phosphinoalkylsilyl complexes with bis- or tris(phosphinoalkyl)silyl. Novel catalysts are also provided which are platinum-group metal complexes with bis- or tris(phosphinoalkyl)silyl ligands, which are synthesized by using novel bis(phosphinoalkyl)silanes or tris(phosphinoalkyl)silanes.

23 Claims, No Drawings

PROCESS FOR CATALYTIC HYDROFORMYLATION

BACKGROUND OF THE INVENTION (a) Field of the Invention

This invention relates to the hydrofromylation of olefins, and to novel catalysts useful in such hydroformylation reactions.

(b) Description of the Prior Art

This process, often referred to as the OXO reaction, involves reaction of olefins with carbon monoxide and hydrogen in the presence of a suitable catalyst. It involves the addition of H and CHO across the double bond of the olefin, hence the term hydroformylation. The aldehyde may be further hydrogenated, either in situ by the same catalyst or in a separate reaction step, as shown in the following reaction scheme:

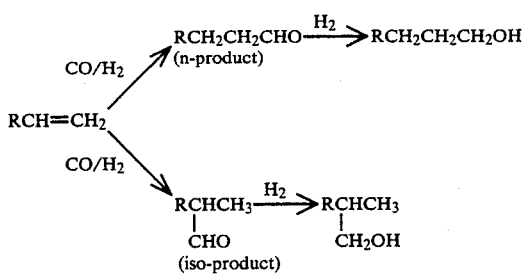

In general, alcohols are the most important products, but aldehydes can be useful chemical intermediates. This is well illustrated in the hydroformylation of propylene, where n-butyraldehyde is both hydrogenated to n-butanol and converted, via aldol condensation, to 2-ethyl-1-hexanol, as shown in the following reaction scheme:

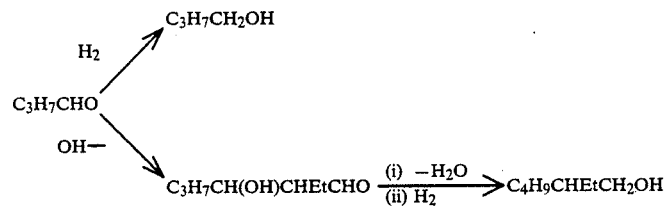

With olefins other than ethylene, a mixture of isomeric aldehydes is produced. From a commercial standpoint, maximum selectivity to the normal, straight-chain product is desirable. The reasons for preferring the n- over the iso- product relate to chemical utility and improved performance in the end product. Thus, in the hydroformylation of propylene, the isobutyraldehyde, readily separable from n-butyraldehyde, is not a useful product and, if present in large amount, may need to be disposed of. For higher molecular weight materials, e.g. $C_8$-$C_{10}$ alcohols used in plasticiser manufacture, typically as diethylphthalates, and $C_{12}$-$C_{16}$ alcohols in detergents, typically as alcohol ethoxylates, $RO(CH_2CH_2O)_xH$, separation is difficult and the product mixture is generally used without purification. For detergents, linear alcohols mimic the natural systems with which they compete, e.g. alcohols derived from coconut oil, and are more easily biodegraded than their branched isomers. Price and performance are however always balancing considerations. Thus, for plasticisers, the branched 2-ethyl-hexanol (from $C_3H_6$ via n-$C_3H_7CHO$) competes with n-octanol (from the more expensive heptene) largely on the basis of cost as a prime consideration.

The hydroformylation reaction was first operated using supported cobalt catalysts, but it is now known that homogeneous systems (using e.g. homogeneous cobalt or rhodium catalysts) are better than heterogeneous ones.

The patent literature is replete with patents alleging improved catalysts for hydroformylation and improved hydroformylation processes. Among those patents, the following non-exhaustive list may be mentioned.

CANADIAN PATENTS (1) 729,213 issued Mar. 1, 1966, to Charles R. Greene and Robert E. Meeker, for PROCESS FOR OLEFIN HYDROFORMYLATION;

(2) 820,341 issued Aug. 12, 1966 to John L. Van Winkle, for HYDROFORMYLATION OF OLEFINS;

(3) 905,988 issued July 25, 1972 to Keith G. Allum, Ronald D. Hancock, Samuel McKenzie and Robert C. Pitkethly, for HYDROFORMYLATION PROCESS;

(4) 951,738 issued July 23, 1974 to Pudens L. Ragg, for HYDROFORMYLATION OF OLEFINS;

(5) 1,022,934 issued Dec. 20, 1977 to Donald E. Morris and Harold B. Tinker, for HYDROFORMYLATION PROCESS;

(6) 1,082,722 issued July 29, 1980 to Jerry D. Unruh and William J. Wells, III, for HYDROFORMYLATION CATALYSTS;

(7) 1,123,859 issued May 18, 1982 to Edward B. Hackman, Larry D. Zeagler, James S. McLaughlin and Carl M. Peabody, for HYDROFORMYLATION PROCESS IMPROVED BY CHOICE OF REACTION SOLVENT AND CONTROL OF PRODUCT STRIPPING PARAMETERS; and (8) 1,191,864 issued Aug. 13, 1985 to Petrus W. N. M. Van Leeuwen and Cornelis F. Roobeek, for PROCESS FOR THE HYDROFORMYLATION OF OLEFINS.

U.S. PATENTS (1) U.S. Pat. No. 3,239,566, patented Mar. 8, 1966 by Lynn H. Slaugh and Richard D. Mullineaux for HYDROFORMYLATION OF OLEFINS; p (2) U.S. Pat. No. 3,278,612, patented Oct. 11, 1966 by Charles R. Greene for OXO PROCESS USING COBALT CARBONYL AND TERTIARY PHOSPHINE UNDER BASIC CONDITIONS;

(3) U.S. Pat. No. 3,310,576, patented Mar. 21, 1967 by Joseph Kern Mertzweiller and Horace Marion Tenney for HYDROFORMYLATION CATALYST AND PROCESS RELATING THERETO;

(4) U.S. Pat. No. 3,515,757, patented June 2, 1970 by John W. Silbert for ORGANIC COMPOUNDS AND PROCESSES;

(5) U.S. Pat. No. 3,576,881, patented Apr. 27, 1971 by William L. Sena, Jr. for PREPARATION OF MODIFIED OXO CATALYST AND PROCESS RELATING THERETO;

(6) U.S. Pat. No. 3,917,661, patented Nov. 4, 1975 by Roy L. Pruett and James A. Smith for HYDROFORMYLATION OF UNSATURATED ORGANIC COMPOUNDS;

(7) U.S. Pat. No. 3,954,877, patented May 4, 1976 by Robert M. Gipson for HYDROFORMYLATION OF OLEFINS;

(8) U.S. Pat. No. 3,965,192, patented June 22, 1976 by Frank B. Booth for HYDROCARBONYLATION PROCESS;

(9) U.S. Pat. No. 3,976,596, patented Aug. 24, 1970 by Marion F. Hawthorne and Timm E. Paxson for HYDRIDOMETALLIC CARBORANE CATALYTIC COMPOUNDS.

(10) U.S. Pat. No. 4,041,082, patented Aug. 9, 1977 by Takeru Omoda and Tetsuo Masuyama for PROCESS FOR PRODUCING ALDEHYDES;

(11) U.S. Pat. No. 4,052,461, patented Oct. 4, 1977, by Harold Burnharm Tinker and Donald E. Morris for HYDROFORMYLATION PROCESS;

(12) U.S. Pat. No. 4,089,881, patented May 16, 1978 by Charles M. Lukehart for COMPLEXES OF METALLATED COORDINATION LIGANDS;

(13) U.S. Pat. No. 4,089,727, patented July 4, 1978 by Werner O. Haag and Dwayne Waichurst for INSOLUBLE POLYMERS HAVING FUNCTIONAL GROUPS CONTAINING CHEMICALLY BONDED GROUP VIII METAL;

(14) U.S. Pat. No. 4,139,565, patented Feb. 13, 1979 by Jerry D. Unruh and Leslie E. Wade for HYDROFORMYLATION USING IMPROVED CATALYSTS COMPRISING RHODIUM AND DIPHOSPHINO LIGANDS;

(15) U.S. Pat. No. 4,155,939, patented May 22, 1979 by John E. Poist for HYDROFORMYLATION PROCESS;

(16) U.S. Pat. No. 4,169,861, patented Oct. 2, 1979 by O. Richard Hughes for HYDROFORMYLATION PROCESS;

(17) U.S. Pat. No. 4,200,592, patented Apr. 29, 1980 by Rosemary R. Hignett and Peter J. Davidson for CATALYTIC HYDROFORMYLATION;

(18) U.S. Pat. No. 4,201,714, patented May 6, 1980 by O. Richard Hughes for STABILIZED CATALYST COMPLEX OF RHODIUM METAL, BIDENTATE LIGAND AND MONODENTATE LIGAND;

(19) U.S. Pat. No. 4,201,728, patented May 6, 1980 by O. Richard Hughes for HYDROFORMYLATION CATALYST AND PROCESS;

(20) U.S. Pat. No. 4,285,215, patented Mar. 24, 1981 by John I. Dawes for HYDROFORMYLATION PROCESS;

(21) U.S. Pat. No. 4,291,196, patented Sept. 29, 1981 by Edwin H. Homeier, Alan R. Dodds and Tamatsu Imai for CATALYST RECOVERY;

(22) U.S. Pat. No. 4,386,013, patented May 31, 1983 by Kenneth P. Callahan, Peter M. DiGiacomo and Martin B. Dines for HYDROFORMYLATION PROCESS UTILIZING NOVEL CATALYST;

(23) U.S. Pat. No. 4,399,312, patented Aug. 16, 1983 by Michael J. H. Russel and Barry A. Murrer for CATALYTIC PROCESS;

(24) U.S. Pat. No. 3,937,742, patented Feb. 10, 1976 by Jin Sun Yoo for HYDROFROMYLATION PROCESS USING CATALYST COMPRISING PLATINUM GROUP METAL ON SUPPORT HAVING SEPARATE ALUMINA PHASE;

(25) U.S. Pat. No. 4,358,621, patented Nov. 9, 1982 by Tadamori Sakakibara, Yoshihisa Matsushima and Katsumi Kaneko for PROCESS FOR PRODUCING ALDEHYDES;

(26) U.S. Pat. No. 4,108,905, patented Aug. 22, 1978 by Geoffrey Wilkinson for CATALYTIC REACTIONS;

(27) U.S. Pat. No. 4,298,541, patented Nov. 3, 1981 by Alexis A. Oswald and Andrew A. Westner, TRIHYDROCARBYL SILYL-SUBSTITUTED ALKYL DIARYL PHOSPHINE TRANSITION METAL COMPLEXES AND THEIR USE AS HOMOGENEOUS CATALYSTS;

(28) U.S. Pat. No. 4,400,548, patented Aug. 23, 1983 by Anthony G. Abatjoglou and Ernst Billig, HYDROFORMYLATION PROCESS USING BISPHOSPHINE MONOOXIDE LIGANDS; and

(29) U.S. Pat. No. 4,450,299, patented May 22, 1984 by Alexis A. Oswald, Torris G. Jermansen, Andrew A. Westner and I-Deo Haang for HOMOGENEOUS HYDROFORMYLATION CATALYSTS WITH SILYL SUBSTITUTED ALKYL DIARYL PHOSPHINE METAL COMPLEXES.

In summary, among the catalysts proposed by the above noted patents are the following: dicobalt octacarbonyl per se or in various modified forms; certain transition metal complexes with biphyllic ligands, e.g. complexes of cobalt with carbon monoxide and tribytyl phosphite or triphenyl phosphine; a metal complex catalyst having incorporated therein a biphyllic ligand, e.g. carbon monoxide in conjunction with other selected biphyllic ligands and in particular phosphines e. g., tributyl phosphine or triphenyl phosphine; cobalt in complex combination with carbon monoxide and tertiary organophosphines; compounds containing transition metals bonded to phosphorus and silicon; a metallated polymer of a styrylphosphine having Group VIII metal atoms coordinated to the phosphorus atoms; an ionic rhodium complex $Rh(CO)_xL_yAn$, the ionic compound comprising a complex cationic rhodium moiety $Rh(CO)_xL_y$ and a non-coordinating anionic moiety An; a Group VIII metal in complex combination with a monodentate or polydentate ligand comprising a triorganophosphine, triorganophosphite, triorganoarsine, or triorganostibine moiety; a ligand-stabilized-platinum-containing catalytic system comprising at least a secondary phosphine oxide moiety; a catalyst comprising ruthenium and/or rhodium in complex combination with carbon monoxide and a phosphorus-containing ligand consisting essentially of a tertiary organo phosphorus compound in which the phosphorus is trivalent; a cobalt carbonyl tri-n-butyl phosphine; a complex which contains a transition metal selected from Group VIII in complex bond with at least one carbon monoxide molecule, at least on biphyllic ligand which contains an atom selected from Group V-A, and a ligand consisting of a conjugated diolefin adduct; a rhodium complex, e.g. hydridocarbonylbis(triphenylphosphine)dichlororhodium; complex metal carbonyl compounds having the generic formula $M_2(CO)_2(XR_3)_2$ wherein M is iron, cobalt or rhodium, X is phosphorus or arsenic, and R is an alkyl or alkoxy radical having from 1 to 20 carbon atoms; rhodium in complex combination with carbon monoxide and a ligand containing a trivalent atom of a Group VA element including phosphorus, arsenic, and antimony; a complex Group VIII catalyst modified by incorporating therein a catalyst modifier of pentavalent phosphorus arsenic or antimony; a catalyst comprising a complex between an organic ligand and a Group VIII noble metal hydride carbonyl; a complex combination of a Group VIII noble metal hydride with carbon monoxide and an organic ligand; a rhodium-tertiary phosphine complex; organometallic complexes which contain at least two metal atoms, or a metal atom and a proton, and at least one ligand representing a metallated unsaturated chelating six-membered ring system, where the metallation involves the formal replacement of a methine group by an organometallic complex; a rhodium catalyst in the form of an ionic rhodium compound, consisting of a rhodium-containing cation having rhodium complexed with ligands other than halide, and a non-coordinating anion; an insoluble polymer containing a functional group, which may be an amine, thiol, phosphine, or arsine group, having chemically bonded thereto a metal of Group VIII; rhodium hydrido carbonyl in complex combination with a diphosphino-substituted ligand; a ligand stabilized complex of platinum dihalide dimer and stannous halide; a stabilized catalyst complex of rhodium metal, bidentate ligand and specified monodentate ligand; a complex of Rh(I) in solution and a homogeneous co-catalyst dissolved in the solution and comprising a co-ordination complex of a transition metal other than rhodium selected from Group 6 or Group 8 of the Periodic Table; metal carbonyls or organometallic complexes in which the metal portion of the complex is selected from Group VIII metal; a composite of rhodium metal or a rhodium metal compound and a compound selected from the group consisting of compounds represented by the general formula $M(O_3ZO_2R)_{12}$, wherein M comprises a tetravalent metal, Z comprises a pentavalent atom, R is selected from the group consisting of organo radicals comprising a moiety selected from the group consisting of phosphine radicals; x is 0 or 1, and n is 2; a catalyst containing a hydrido-platinum group metal-carbonyl, e.g. hydridopalladium carbonyl, on a solid, acidic, silica-based support material, also containing a Group VA electron donor ligand, e.g. triphenyl phosphine; a Pt Group IV-A organometallic catalyst mixture, e.g. $(PPh_3)_2PtPhSnPh_2Cl/SnCl_2$; a hydrido carbonyl complex of rhodium which includes two phosphorus-containing stabilizing donor ligands selected from the group consisting of triphenyl phosphine an triphenylphosphite; homogeneous trihydrocarbyl silyl-substituted alkyl diaryl phosphine transition metal complexes of the general formula: $[(AR_2PPO)_3SiR_4]_g(MX_n)_y$, wherein Ar is a $C_6$ to $C_{10}$ aromatic hydrocarbyl radical, Z is a $C_3$ to $C_{30}$ saturated straight chain divalent radical, R is an unsubstituted $C_1$ to $C_{10}$ hydrocarbyl, $C_1$ to $C_{10}$ monosubstituted hydrocarbyl phenyl radical, y is 1 to 4, g times y is 1 to 6, M is a transition metal selected from the group consisting of Group VIII transition metals, X is an anion or organic ligand excluding halogen satisfying the coordination sites of the metal, n is 2 to 6 and s is 1 to 3; and trihydrocarbyl silyl-substituted alkyl diaryl phosphine transition metal complexes.

SUMMARY OF THE INVENTION (a) Aims of the Invention

In spite of all these patented catalysts which were said to have solved myriad problems in hydroformylation processes, including improving catalyst stability, improving catalyst activity by avoiding the necessity for the use of exceedingly high pressures, speeding up the slow rate of hydroformylation while maintaining high selectivity at temperatures conducive to high conversion levels and high reaction rates, the improvement of the linear/branched product ratio, or to provide soluble catalysts, there remains a need for hydroformylation catalysts and processes which provide for olefin conversion to aldehyde products with improved efficiency and selectivity at lower carbon monoxide pressures, and with a concomitant reduction in the yield of isomerization, hydrogenation, and polymerization products.

Several of the above patents refer to the use, as ligands, of compounds containing P and Si connected by one or more $CH_2$ groups. Specifically, the above patents appear to deal exclusively with metal complexes in which the phosphinoalkylsilyl fragment is attached through P only, rather than in a cyclic unit attached by P and Si as in the complexes used in the hydroformylation process of aspects of the present invention which will be discussed in detail later.

One object of the present invention is the provision of an improved hydroformylation process enabling the more efficient production of desired products by rapid hydroformylation reactions of olefinic compounds with carbon monoxide and hydrogen in the presence of a new and improved hydroformylation catalyst.

Still another object of the present invention is the provision of an improved hydroformylation process enabling the efficient single stage production of aldehydes by reaction of olefinic hydrocarbons with carbon monoxide and hydrogen in the presence of an improved and more stable catalyst, facilitating product isolation, catalyst recovery, and recycle steps without substantial decomposition and loss.

Yet another object of this invention to provide a novel hydroformylation catalyst which promotes the conversion of olefins to aldehydes with a high rate of reaction and a high level of conversion.

A further object of this invention is to provide an improved hydroformylation process for converting alpha-olefins to linear aldehydes with improved efficiency and selectivity.

(b) Statements of Invention

By this invention, a novel hydroformylation process is provided for the conversion of an having up to about 20 carbon atoms to a corresponding aldehyde, which process comprises: reacting the olefinic compound in the liquid phase with carbon monoxide and hydrogen at a temperature between about 60° and about 200° C. and at a pressure of up to about 1000 psi or more in the presence of a catalyst comprising a chelate in which a ligand is chelated at a metal center to produce at least one heterocyclic ring with the central metal atom as part of the ring, the catalyst being selected from the group consisting of (A) a platinum group metal complex of bis (phosphinoalkyl)silane having the following Formula I:

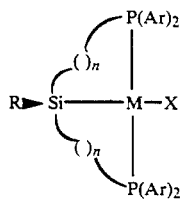

Formula I wherein:
Ar is alkyl, phenyl or modified aryl, cyclohexyl or C$_6$H$_4$X
X is Cl, Br, F, CO$_2$CF$_3$, or SnCl$_3$;
R is Me, Et, n-Br, t-Bu or cyclohexyl or phenyl;
M is an operative metal selected from the group consisting of Pt, Pd, Rh, and Ir; and
( )$_n$ is 2, 3, or 4, thereby to provide 2, 3 or 4 C atoms respectively between Si and P:

(B) a platinum-group metal complex having the Formula II

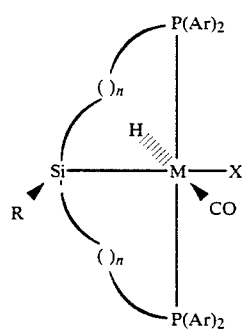

Formula II wherein Ar, X, R, M and ( )$_n$ are as defined above;

(C) a platinum-group metal complex having the Formula III

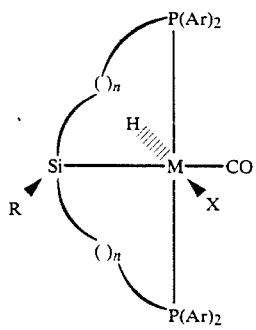

Formula III wherein Ar, X, R, M and ( )$_n$ are as defined above;

(D) a platinum-group metal complex having the Formula IV

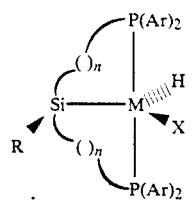

Formula IV wherein Ar, X, R, M and ( )$_n$ are as defined above;

(E) a platinum-group metal complex of the Formula V

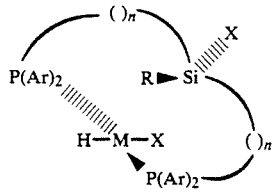

Formula V (F) a platinum-group metal complex of the Formula VI

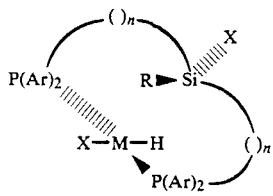

Formula VI wherein Ar, X, R, M and ( )$_n$ are as defined above;

(G) a platinum-group metal complex of tris(phosphinoalkyl) silane having the following Formula VII

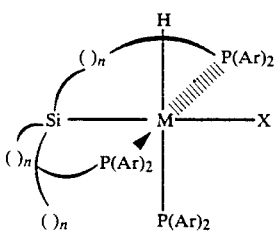

Formula VII wherein Ar, X, M and ( )$_n$ are as defined above;

(H) a platinum-group metal complex having the Formula VIII

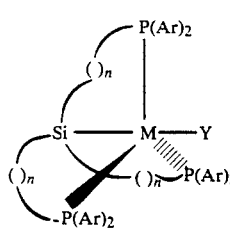

Formula VIII wherein Ar, M and ( )$_n$ are as defined above, and Y=CO, P(Ar)$_3$, or a similar neutral ligand molecule;

(I) a platinum-group metal complex of the Formula IX

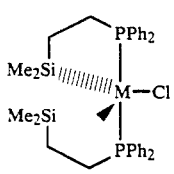

Formula IX (J) a platinum-group metal complex of the Formula X

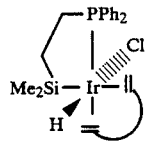
(K) a platinum-group metal complex of the Formula XI
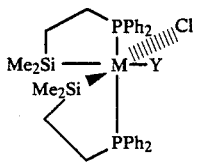
(L) a platinum-group metal complex of the Formula XII
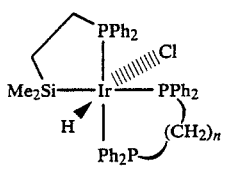
(M) a platinum-group metal complex of the Formula XIII
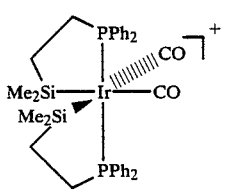
and
(N) a platinum-group metal complex of the Formula XIV
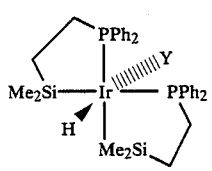
Specific embodiments of the catalysts used in the abovedescribed hydroformylation process of this invention include the following:
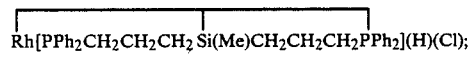
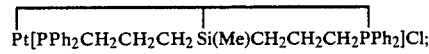
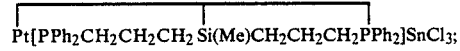
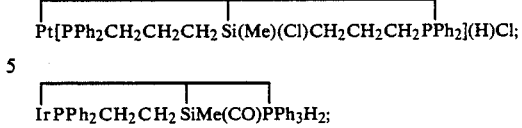
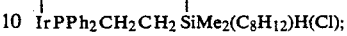
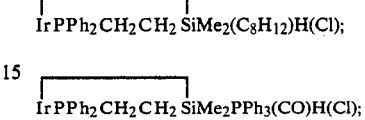
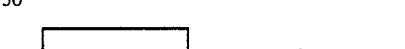
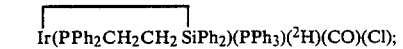
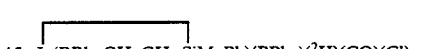
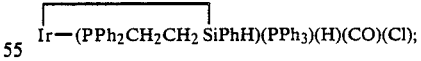
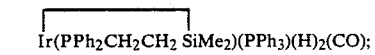

[Rh(PPh₂CH₂CH₂SiMe₂)₂Cl];

Ir(PPh₂CH₂CH₂SiMe₂)₂Cl;

[Rh(PPh₂CH₂CH₂SiMe₂)₂Br];

[Rh(PPh₂CH₂CH₂SiMe₂)₂I];

[Ir(PPh₂CH₂CH₂SiMe₂)₂Br];

[Ir(PPh₂CH₂CH₂SiMe₂)₂I];

[Ir(PPh₂CH₂CH₂SiMe₂)(COD)(H)(Cl)];

[Ir(PPh₂CH₂CH₂SiMe₂)(Ph₂PCH₂CH₂PPh₂)(H)(Cl)];

[Ir(PPh₂CH₂CH₂SiMe₂)(PPh₂CH₂PPh₂)(H)(Cl)];

[Rh(PPh₂CH₂CH₂SiMe₂)₂(Cl)(CNBuᵗ)];

[Rh(PPh₂CH₂CH₂SiMe₂)₂(Cl)(CNCMe₃CMe₃)];

[Rh(PPh₂CH₂CH₂SiMe₂)₂(Cl)(CNCHMe₂)];

[Ir(PPh₂CH₂CH₂SiMe₂)₂(Cl)(CO)];

[Ir(PPh₂CH₂CH₂SiMe₂)₂(Cl)(PF₃)];

[Ir(PPh₂CH₂CH₂SiMe₂)₂(Cl)(P{OMe}₃)];

[Ir(PPh₂CH₂CH₂SiMe₂)₂(Cl)(P{OEt}₃)];

[Ir(PPh₂CH₂CH₂SiMe₂)₂(Cl)(CNBuᵗ)];

[Ir(PPh₂CH₂CH₂SiMe₂)₂(Cl)(CNCMe₂CH₂CMe₃)];

[Ir(PPh₂CH₂CH₂SiMe₂)₂(Cl)(CNCHMe₂)];

[Ir(PPh₂CH₂CH₂SiMe₂)₂(CO)₂]BF₄;

[Ir(PPh₂CH₂CH₂SiMe₂)₂(H)(CO)];

[Ir(PPh₂CH₂CH₂SiMe₂)₂(H)(CNBuᵗ)];

Rh[PPh₂CH₂CH₂CH₂Si(Me)CH₂CH₂CH₂PPh₂](H)(Cl);

Pt[PPh₂CH₂CH₂CH₂Si(Me)CH₂CH₂CH₂PPh₂]Cl;

Pt[PPh₂CH₂CH₂CH₂Si(Me)CH₂CH₂CH₂PPh₂]SnCl₃;

Pt[Ph₂PCH₂CH₂Si(Me)₂](PPh₃)(Cl)

Pt[Ph₂PCH₂CH₂Si(Me)₂](Ph₂PMe)(Cl)

Rh[Si(CH₂CH₂PPh₂)₃](H)(Cl)

Rh[Si(CH₂CH₂PPh₂)₃](CO)

Rh[Si(CH₂CH₂PPh₂)₃]

Rh[Si(CH₂CH₂PCy₂)₃](H)(Cl)

Rh[Si(CH₂CH₂PCy₂)₃](CO)

Rh[Si(CH₂CH₂PPh₂)₃](H)(SnCl₃)

Ir[Si(CH₂CH₂PPh₂)₃](H)(Cl)

Ir[Si(CH₂CH₂PPh₂)₃](H)(SnCl₃)

Ir[Si(CH₂CH₂PPh₂)₃](CO)

Ir[Si(CH₂CH₂CH₂PPh₂)₃](H)(Cl)

Ir[Si(CH₂CH₂CH₂PPh₂)₃](CO)

Rh[Si(CH₂CH₂CH₂PPh₂)₃](H)(Cl)

Rh[Si(CH₂CH₂CH₂PPh₂)₃](CO)

Pt[PPh₂CH₂CH₂CH₂Si(Me)(Cl)CH₂CH₂CH₂PPh₂](H)Cl;

Ir PPh₂CH₂CH₂SiMe₂(CO)PPh₃H₂;

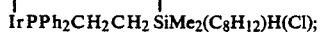

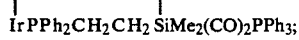

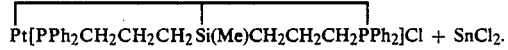

With respect to the olefins which may be subjected to the hydroformylation process of the present invention, in general α-olefins, although more expensive than the counterpart internal olefins, are the preferred feedstocks in that they give a much higher proportion of the desired linear product.

With olefins higher than propylene, it was found that catalysts used heretofore may tend to isomerise the double bond along the hydrocarbon chain and this may lead to the production of a number of additional branched products.

The unsaturated carbon-to-carbon olefinic linkages may be between terminal and their adjacent carbon atoms, as in 1-pentene, or between internal chain carbon atoms, as in 4-octene. It may also be possible to use olefinic hydrocarbon fractions. If desired, suitable such feeds consisting of olefinic hydrocarbon fractions include, for example, $C_7$, $C_8$, $C_9$, $C_{10}$ and higher olefinic fractions as well as olefinic hydrocarbon fractions of wider boiling ranges, e.g. $C_{7-9}$, $C_{10-13}$, $C_{14-17}$ olefinic hydrocarbon fractions and the like.

According to the present invention, examples of useful olefins include the following: ethylene, propylene, butylene, butylene, butene-1, butene-2, pentene-1, benzenes, 2-methylbutene-1, cyclobutene, hexene-1, hexene-2, heptenes, ethyl pentenes, octenes, decenes, nonenes, dodecene, 1-octadecene, dihydronaphthalene, cyclohexene, 3-ethylhexene-1, isobutylene, octene-1, 2-propylhexene-1, ethylcyclohexene, decene-1, cycloheptene, cyclooctene, cyclononene, cyclodecene, cyclododecene, 2-ethyl-1-hexene, styrene, 3-phenyl-1-propene, allyl chloride, 1,4-chloride, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl 7-octenoate, 3-butenoic acid, 7-octenoic acid, 3-butenenitrile, 5-hexenamide, 4,4'-dimethylnonenedodecene-1, undecene-3, 6-propyldecene-1, tetradecen-2, 7-amyldecene-1, oligomers of olefins, e.g. propylene tetramer, ethylene trimer, etc., hexadecene-1, 4-ethyltridecene-1, octadecene-1, 5,5-dipropyldocecene-1, vinylcyclohexane, allylcyclohexane, styrene, p-methylstyrene, alpha-methylstyrene, p-vinylcumene, beta-vinylnaphthanene, 1,1-diphenylethylene, allylbenzene, 6-phenylhexene-1, 1,3-diphenylbutene-1, 3-benzylheptene-1, o-vinyl-p-xylene, divinylbenzene, 1-allyl-4-vinylbenzene, 1,3-butadiene, 1,4-pentadiene, 1,5-hexadiene, 1,4-heptadiene, 1,7-octadiene, 2,6-decadiene, 1,9-dodecadiene, 1,5-hexadiene, 1,4-heptadiene, 1,7-octadiene, 2,6-decadiene, 1,9-dodecadiene, 1,5-hexadecadiene, 1,4,7-octatriene, 1,4,7,10-undecatetraiene, 1,4-cycloheptadiene, 1,5-cyclooctadiene, 1,4,7-cycloderatriene, 1,5,9-cyclododecatriene, 1,5-bicyclo(2,2,2)heptadiene, 1,2-butadiene, 1,3,5-hexatriene, 2-chloro-1,3-butadiene, 2-chloro-1,3-butadiene, 3,5-monodacadiene, 1,5-hexadiene, 1,5,8-dodecatrriene, and 2,6-octadecadiene.

Of the preceeding examples, the alpha olefins and olefins having 2 to 8 carbons are preferred classes. It is preferred to use internal normal olefins, having, for example, from 4 to 19 carbon atoms to the molecule to normal terminal alcohols having 5 to 20 carbon atoms to the molecule respectively. A characteristic feature of olefins with two or more double bonds is that only one of the double bonds is hydroformylated. The remaining double bonds are hydrogenated. Preferred alpha olefinic compounds include alkenes, alkyl alkenoates, especially those which contain up to about 20 carbon atoms.

Process operating parameters employed in the process of the present invention will vary depending upon the nature of the end product desired. In general, however, the operating parameters contemplated by the process of aspects of the present invention are the same as those conventionally employed in prior art hydroformylation processes.

The preferred hydroformylation process of this invention will be that process which is most efficient in producing normal aldehyde isomer product, i.e. straight chain aldehyde as distinguised from its isomeric or branched chain aldehyde product. The optimization of the reaction conditions necessary to achieve the best results and efficiency desired will be well within the knowledge of one skilled in the art and easily obtainable by following the more preferred embodiments of this invention as explained more fully below and/or by simple routine experimentation.

In general, the hydroformylation process of this invention is conducted under a total pressure of hydrogen and carbon monoxide up to and exceeding about 250 atmospheres; the pressure is usually kept as low as possible for economic reasons. Pressures in the range of about 50 psig to about 3,000 psig, (about 50 to about 150 atmospheres) are generally satisfactory. For commercial reasons, however, pressures significantly greater than about 400 psig will not normally be employed.

The total gas pressure of hydrogen, carbon monoxide and olefinic unsaturated compound of the hydroformylation process of aspects of this invention may range from about 1 to about 10,000 psig. More preferably however the process of this invention is operated at low pressures the preferred total gas pressure of hydrogen, carbon monoxide and olefinic unsaturated compound being less than about 1500 psia, more preferably less than about 500 psia and most preferably less than about 350 psia. The minimum total pressure of the reactant gases is not particularly critical and is limited predominantly only by the amount of reaction gases necessary to obtain a desired rate of reaction. The preferred carbon monoxide partial pressure of the process of aspects of this invention is preferably less than about 200 psia, more preferably less than about 100 psia and most preferably from about 1 to about 50 psia. On the other hand, the partial pressure of hydrogen gas of the hydroformylation process of this invention is preferably less than about 500 psia, more preferably less than about 400 psia and most preferably about 20 to about 200 psia. In addition it is generally preferred that the partial pressure of carbon monoxide be less than about 75% of the total gas pressure of (CO+H$_2$). However in certain instances it may be plausible to increase the carbon monoxide partial pressure to a value above about 75% of the total gas pressure. On the other hand, in general, a partial pressure attributable to hydrogen of from about 25 to about 95% and more, based on the total gas pressure of (CO+H$_2$) should be suitable in most instances. It is further normally advantageous to employ a total gas pressure in which the partial pressure attributable to hydrogen is greater than the partial pressure attributable to carbon monoxide, e.g. a H$_2$/CO molar ratio of gaseous hydrogen to carbon monoxide within any range from about 3:2 to about 200:1 or higher, the more preferred hydrogen to carbon monoxide molar ratio being from about 3:1 to about 20:1.

The other hydroformylation reaction conditions are well known to those skilled in the art and are variable over wide ranges of temperatures and pressures. In the practice of the process of this invention, the temperatures may range between from about 100° C. and about 200° C. The process according to the present invention is carried out under mild reaction temperature conditions. Temperatures in the range of from about 50° C. to about 200° C. can be suitably applied, but lower or higher temperatures can also be used. Preference is given to temperatures in the range of from about 75° C. to about 150° C.

Preferred space velocities are an olefin LHSV of from about 0.1 to about 20 and GHEV of hydrogen and carbon monoxide of about 50 to about 10,000. The lHSV or GHSV is expressed as volumes of liquid or gas per vol. of catalyst.

A reaction time between about 2 and about 5 hours is particularly preferred. The reaction may be operated batchwise or continuously.

Catalyst concentrations are not generally critical, provided that they are such that the reaction proceeds at an acceptable rate. In practice, the upper limit of concentration is dictated by economic considerations. Molar ratios of catalyst to olefin in the reaction zone at any given instant between about 1:1000 and about 10:1 are found to be satisfactory; higher or lower catalyst to olefin ratios may, however be used, e.g. between about 12:1 and about 1:12, but in general it will be about 1:1.

The ratio of hydrogen to carbon monoxide charged may vary widely. The ratio of hydrogen to carbon monoxide can vary broadly over a mole ratio range between about 30:1 and about 1:30. The average mole ratio will vary between about 10:1 and about 1:10. The quantity of hydrogen/carbon monoxide charged should be at least sufficient to satisfy the stoichiometric requirements of the olefin hydroformylation system. In general, a mole ratio of hydrogen to carbon monoxide of at least about 1 is employed. Suitable ratios of hydrogen to carbon monoxide comprise those within the range of from about 1 to about 10. Higher or lower ratios may, however, be employed. The ratio of hydrogen to carbon monoxide preferably employed will be governed to some extent by the nature of the reaction product desired. If conditions are selected that will result primarily in an aldehyde product, only one mole of hydrogen per mole of carbon monoxide enters into reaction with the olefin.

Excess carbon monoxide or hydrogen over the above-described stoichiometric amounts, however, may be present. Any ratio of H$_2$ to CO from about 10:1 to about 1:10 may be chosen. The preferred ratio is about 1:1 which encourages aldehyde formation.

Some of the complexes used as hydroformylation catalysts are novel per se. Other complexes have been disclosed by the present inventors, but their utility as hydroformylation catalysts have not been suggested. These disclosures include the following:

(1) "Phosphinoalkylsilanes: Synthesis and Spectroscopic Properties of Phosphino(silyl) methanes, 1-Phosphino-2-silylethanes, and 1-Phosphino-3-silylpropanes". Rupert D. Holmes-Smith, Rexford D. Osei, and Stephen R. Stobart, J. Chem. Soc. Perkin Trans. 1 1983;

(2) "(Phosphinoalkyl)silyl Complexes. 3. Chelate-Assisted Hydrosilylation: Formation of Enantiomeric and Diastereoisomeric Iridium (III) Complexes with Chelating (Phosphinoethyl)silyl Ligands". Mary J. Auburn, Rupert D. Holmes-Smith, and Stephen R. Stobart. Journal of the American Chemical Society, 1984, 106, 1314;

(3) "Intramolecular Rearrangement Behaviour of a Dihydridoiridium (III) Complex formed by Regiospecific Chelate-assisted Hydrosilylation". Mary J. Auburn and Stephen R. Stobart. Journal of the Chemical Society Chemical Communications 1984;

(4) "Phosphinoalkylsilyl Complexes. 6. Isolation of a Silyl Complex of Iridium (I). Crystal and Molecular Structure of Dicarbonyl(triphenylphosphine)-[((diphenylphosphino)ethyl)-dimethylsilyl]iridium".
Mary J. Auburn, Stephen L. Grundy, Stephen R. Stobart, and Michael J. Zaworotko, J. Am. Chem. Soc. 1985, 107, 266–267; and (5) "Phosphinoalkylsilyl Complexes, 5, Synthesis and Reactivity of Congeneric Chelate-Stabilized Disilyl Complexes of RH (III) and IF (III); Chlorobis[Diphenylphosphinoethyl-(Dimethyl)Silyl]-Rhodium and -Iridium." Mary J. Auburn, and Stephen R. Stobart, Inorg. Chem. 24, 318–323 1985.

DESCRIPTION OF PREFERRED EMBODIMENTS

The following Experiments and Examples are given to illustrate the present invention.

EXPERIMENT 1

A series of phosphino(silyl)methanes, 1-phosphino-2-silylethanes and 1-phosphino-3-silylpropanes was prepared according to the procedures described in the above-identified Perkin Trans. I 1983, 861.

The compounds prepared had the following structures:

| (A) | (B) | (C) |
|---|---|---|
| Ph$_2$PCH$_2$SiXYZ | Ph$_2$PCH$_2$CH$_2$SiXYZ | |
| (1) X = Y = Z = Me | (11) X = Y = Me, Z = Cl | |
| (2) X = Y = Me, Z = Cl | (12) X = Y = Me, Z = H | |
| (3) X = Y = Me, Z = H | (13) X = Me, Y = Ph, Z = Cl | |
| (4) X = Me, Y = Ph, Z = Cl | (14) X = Me, Y = Ph, Z = H | |
| (5) X = Me, Y = Ph, Z = H | (15) X = Y = Ph, Z = Cl | |

-continued

|   |   |   |
|---|---|---|
| $R_2Si\frown PR_2$ | $R_2Si\underset{M}{\overset{\frown}{\diagup}}PR_2$ | $R_2Si\underset{M}{\overset{\frown}{\diagup}}PR_2$ |
| M  M | | |
| (A) | (B) | (C) |

| | |
|---|---|
| (6) X = Y = Ph, Z = Cl | (16) X = Y = Ph, Z = H |
| (7) X = Y = Ph, Z = H | (17) X = Me, Y = Z = Cl |
| (8) X = Y = Z = Ph | (18) X = Me, Y = Z = H |
| (9) X = Ph, Y = Z = Cl | (19) X = Ph, Y = Z = Cl |
| (10) X = Ph, Y = Z = H | (20) X = Ph, Y = Z = H |
| | (21) X = Y = Z = Cl |
| | (22) X = Y = Z = H |

| $Ph_2PCH_2CH_2CH_2SiXYZ$ | $Me_2PCH_2CH_2SiXYZ$ |
|---|---|
| (23) X = Y = Z = Me | (28) X = Y = Me, Z = Cl |
| (24) X = Y = Me, Z = Cl | (29) X = Me, Y = Ph, Z = Cl |
| (25) X = Y = Me, Z = H | (30) X = Me, Y = Z = Cl |
| (26) X = Y = Z = Cl | (31) X = Y = Me, Z = H |
| (27) X = Y = Z = H | (32) X = Me, Y = Ph, Z = H |
| | (33) X = Me, Y = Z = H |

The general synthesis process may be described as follows:

All synthetic manipulations were carried out using standard inert atmosphere techniques and all solvents were dried and distilled under dry dinitrogen gas. N.m.r. spectra were obtained with Perkin-Elmer R32 ($^1H$, 90 MHz), Nicolet TT-14 ($^{13}C$, 15.1 MHz; $^{31}P$, 24.3 MHz), and Bruker WM250 ($^1H$, 250 MHz; $^{13}C$, 93.6 MHz) spectrometers, I.r. spectra were recorded using a Perkin-Elmer 283 spectrophotometer.

The simple silanes, diphenylphosphine, and methyl-diphenyl-phosphine were purchased (Aldrich, Strem Chemicals, or Petrarch) or synthesized by literature procedures and were distilled under dry dinitrogen gas immediately prior to use. The lithium salt $LiCH_2PPh_2tmeda$ (tmeda = tetramethylethylenediamine) was prepared from methyldiphenylphosphine. Most of the new compounds deteriorated rapidly in air, the chlorosilyl derivatives being particularly sensitive. Purity of products was established by microanalysis.

EXPERIMENT 1

The following are typical of the preparative reactions.

(i) 2-Chlorodimethylsilyl-1-diphenylphosphinoethane (11)

Diphenylphosphine (1.96 g, 1.05 mmol) and chlorodimethylvinyl-silane (2.17 g, 1.66 mmol) were loaded into a quartz reaction tube fitted with a greaseless high-vacuum stopcock, which was then evacuated, placed approximately 5 cm from a medium-pressure mercury lamp and irradiated (5 h). The viscous oily liquid phase was separated from a small quantity of solid material by dissolution in dry benzene (20 cm$^3$). The solution was transferred to a Schlenk tube from which all volatile material was removed by pumping at 20° C./10$^2$ mmHg; the remaining fraction was evaporated (145°–150° C., 10$^2$ mmHg) onto a water-cooled finger to give the colourless liquid product (11)(2.30 g, 7.51 mmol, 71%).

(ii) 2-Dimethylsilyl-1-diphenylphosphinoethane (12)

To a solution of compound (11) (2.25 g, 7,.34 mmol) in dry Et$_2$O (20 cm$^3$) in a Schlenk tube was added LiAlH$_4$ (excess) and the reaction mixture was stirred at 20° C. After 2 h, all volatiles were removed under reduced pressure and the fraction evaporating at 130°–135° C./10$^2$ mmHg was collected yielding the colourless liquid product (12)(1.66 g, 6.09 mmol, 83%).

(iii) Chlorodimethylsilyl(diphenylphosphino)methane (2)

Dichlorodimethylsilane (80 cm$^3$) in tetrahydrofuran (THF) (150 cm$^3$) was cooled to −78° C. and treated dropwise (2 h) with a solution of Ph$_2$PCH$_2$Li.tmeda (10.0 g, 31 mmol) in THF (30 cm$^3$). The mixture was warmed to ambient temperatures and all volatile material was removed under reduced pressure after which the residue was extracted with hexane (3×40 cm$^3$ then 3×20 cm$^3$). The extracts were combined, the solvent removed under reduced pressure, and the product evaporated (125°–130° C.) to give, on a water-cooled probe, the colourless liquid product (2) (6.4 g, 22 mmol, 7.1%).

(iv) Dimethylsilyl(diphenylphosphino)methane (3)

Compound (2) (3.4 g, 12 mmol) was added dropwise to a suspension of LiAlH$_4$ (0.40 g, 10 mmol) in Et$_2$O (20 cm$^3$). The mixture was stirred at 20° C. (1 h), then all volatiles were removed under reduced pressure and the residue was extracted with hexane (6×15 cm$^3$). The extracts were combined and the hexane removed, and the colourless, liquid product (3) (2.5 g, 10 mmol, 83%) was collected after evaporation at 115°–120° C. by condensing it on a water-cooled finger.

(v) 3-Chlorodimethylsilyl-1-diphenylphosphinopropane (24)

Diphenylphosphine (2.20 g, 12.0 mmol) and allyl-dimethylchlorosilane (2.20 g, 16.0 mmol) were allowed to react in an evacuated quartz tube (8 h) under irradiation from a medium-pressure mercury lamp (ca. 5 cm distant). The product mixture was taken up in dry benzene (20 cm$^3$), transferred to a Schlenk tube, and the benzene and excess of silane were removed under reduced pressure. Material evaporating from the residue at 180°–190° C./10$^2$ mmHg was identified as the oily liquid product 924) (2.08 g, 6.48 mmol, 41%).

(vi) 3-Dimethylsilyl-1-diphenylphosphinopropane (25)

Compounds (24) (1.00 g, 3.12 mmol), dry Et$_2$O (20 cm$^3$), and LiAlH$_4$ (excess) were stirred together at 20° C. (1 h) in a Schlenk tube. After the solid had settled, the supernatant layer was recovered by syringe; volatiles were removed under reduced pressure and the colourless liquid product (25) (0.81 g, 2.82 mmol, 90%) evaporated (150°–160° C./10$^2$ mmHg) and collected as before.

(vii) 2-[$^2H_6$]Dimethylsilyl-1-diphenylphosphinoethane[$^2G_6$]-(12)

Repetition of reaction (ii) using LiAlD$_4$ gave the product (84%) with >95% incorporation (i.r.) of $^2H$.

(viii) 1-Diphenylphosphino-2-phenylsilylethane (20)

Irradiation (4 h) of a mixture of Ph$_2$PH (1.09 g, 5.86 mmol) and H$_2$Si(CH:CH$_2$)Ph (0.79 g, 5.90 mmol) yielded after work-up as in (i)–(vi), the product (20) (1.18 g, 3.69 mmol, 63%).

EXPERIMENT 2

A series of phosphinoalkyl(silyl) complexes was prepared according to the description in the above-identified J. Am. Chem. Soc. 1984, 106, 1314; J. Chem. Soc., Chem. Commun. 1984, 281; Inorg. Chem. 1985, 24, 318; and J. Am. Chem. Soc., 1985, 107, 266. publications.

Experiment 1, above, described the preparation of the phosphinoethylsilanes Ph$_2$PCH$_2$CH$_2$SiR$^1$R$^2$H (R$^1$=R$^2$=Me or Ph; or R$^1$=Me, R$^2$=Ph) and Ph$_2$PCH$_2$CH$_2$SiRH$_2$ (R=Me or Ph) by LiAlH$_4$ reduction of the corresponding chloro(phosphinoethyl)silanes. In several cases, the monodeuterio- analogues were obtained similarly, using LiAl$^2$H$_4$. The iridium(I) complexes trans-Ir(Cl)(CO)(PPh$_3$)$_2$ and HIr(CO)(PPh$_3$)$_3$ are readily accessible by using straightforward literature methods.

The following Experiment 2 describes the synthesis of [phosphinoethyl)silyl]iridium(III) complexes.

(1a)

To a stirred solution of trans-Ir(Cl)(CO)(PPHh$_3$)$_2$ (0.50 g, 0.64 mmol) in benzene (40 mL) was added liquid Ph$_2$PCH$_2$CH$_2$SiMe$_2$H drop by drop with a syringe until the characteristic lemon-yellow color of the iridium(I) complex was completely discharged. After further stirring for 10 min, the solvent was pumped away leaving a colorless oily residue, which was dissolved in boiling hexane (35 mL). After the solution was cooled, a white solid separated from which the supernatant was carefully removed and discarded; recrystallization four times from dichloromethane/hexane mixtures afforded the product as a pure white powder, mp 160°–161° C. (0.37 g, 0.47 mmol, 73%). Anal. Calcd for C$_{35}$H$_{36}$ClIrOP$_2$Si: C, 53.18; H, 4,56. Found: C, 52,98; H 4,67. Repeated efforts to crystallize this compound deliberately were unsuccessful; however, on one occasion well-formed colorless cube-shaped crystals which proved to be suitable for X-ray diffraction were obtained fortuitously by dissolution of the oily crude product (ca. 1.0 g) in a large excess (ca. 25 mL) of diethyl ether, followed by addition of an equal volume of hexane and exposure of the resulting clear solution to a rapid draught of cool air.

(1b)

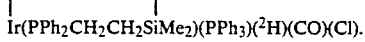

The deuterio analogue (1b) of complex (1a) was prepared by treatment of a benzene solution of trans-Ir(Cl)(CO)(PPh$_3$)$_2$(0.10 g, 0.13 mmol) with just sufficient Ph$_2$PCH$_2$CH$_2$SiMe$_2$$^2$H to cause decolorization of the former. The white product was recovered as described above. (2a)

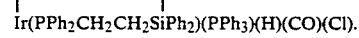

Addition of a solution in benzene of Ph$_2$PCH$_2$CH$_2$SiPh$_2$H to a stirred solution in benzene (15 ml) of trans-Ir(Cl)(CO)(PPh$_3$)$_2$ (0.20 g, 0.26 mmol) until the reaction mixture was completely colorless was followed by removal of solvent. The white residue was washed with hexane (4×10 mL), after which crystallization from dichloromethane/heptane (4×10 mL), after which crystallization from dichloromethane/heptane afforded white microcrystals of the product, (2a) mp 174°–176° C. (0.17 g, 0.19 mmol, 72%). Anal. Calcd for C$_{45}$H$_{40}$ClIrOP$_2$Si: C, 59.11; H, 4,38. Found: C, 58.26; H, 4.66.

(2b)

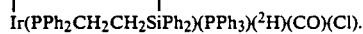

After dropwise addition of a solution in benzene of Ph$_2$PCH$_2$CH$_2$SiPh$_2$$^2$H to a stirring solution in the same solvent (15 mL) of trans-Ir(Cl)(CO)(PPh$_3$)$_2$ (0.10 g, 0.13 mmol) until the yellow color of the latter was discharged completely, the volume of the reaction mixture was reduced to 5 mL, and then heptane (15 mL) was added. The resulting white precipitate (2b) was thoroughly washed with heptane, then dried in vacuo to give the product as a fine white powder (0.08 g, 0.09 mmol, 67%).

(3a)

To trans-Ir-(Cl)(CO)(PPh$_3$)$_2$ (0.10 g, 0.13 mmol) dissolved in toluene (50 mL) and stirred at 60° C. was added liquid Ph$_2$PCH$_2$CH$_2$SiMePhH until complete decolorization occurred, after which stirring of the reaction mixture was continued for 10 min and then solvent was removed to leave a colorless oil. Addition of pentane precipitated a white solid from which was recrystallized (dichloromethane/pentane) the product, (3a) mp 112°–115° C. (0.72 g, 0.09 mmol, 65%), Anal. Calcd for C$_{40}$H$_{38}$ClIrOP$_2$Si: C, 56.38; H, 4.46. Found: C, 57.62; H, 4,81.

(3b)

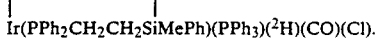

An identical procedure with that described above was followed using deuteriosilane Ph$_2$PCH$_2$CH$_2$SiMePh$^2$H to yield the $^2$H-analogue (4a)

(4b)

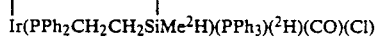

and (5)

These compounds were synthesized in experiments similar to those described above reacting Vaska's complex with the precursors Ph$_2$PCH$_2$CH$_2$SiMe$_n$H$_2$ (n=1 or 2) or Ph$_2$PCH$_2$CH$_2$SiPhH$_2$, respectively. Yields were ca. 50% with mp 80°–85° C. (4a, 4b) or 100°–105° C.(5); the colorless products were characterized by IR and NMR spectroscopy.

(6)

Method A From Complex (1a)

Complex (1a) (0.25 g, 0.32 mmol) was dissolved in THF (10 mL). After dropwise addition of a solution of LiAlH$_4$ (0.14 g, 3.7 mmol) in THF (15 mL) the reaction mixture was stirred overnight and then refluxed (8 h). Careful addition of MeOH to the resulting pale yellow solution afforded a colorless mixture from which all volatiles were removed. The solid residue was redissolved in the minimum of THF and filtered under a N$_2$ atmosphere through a plug of alumina. Slow addition of hexane precipitated the product (6) as a cream-colored powder, ca. 60% yield. Anal. Calcd for C$_{35}$H$_{37}$IrOP$_2$Si: C, 55.64; H, 4.90. Found: C, 55,95; H, 5.10.

Method B From HIr(CO)(PPh$_3$)$_3$

To a solution of HIr(CO)(PPh$_3$)$_3$ (0.10 g, 0.11 mmol) in THF (10 mL) was added Ph$_2$PCH$_2$CH$_2$SiMe$_2$H (0.05 g, 0.18 mmol) dissolved in THF (8.5 mL). After stirring at ambient temperature for 60 min, during which time the reaction mixture became almost colorless, the THF was pumped away, and the residue was taken up in hexane (10 mL). Filtration to give a clear solution was followed by concentration to half volume and refrigeration (−20° C.). Colorless crystals of the product formed over 4 days (0.06 g, 0.08 mmol, 71%) and were shown to be identical with the material prepared by method A using IR and NMR spectroscopy.

(7)

This compound was shown to be the major product of reactions in refluxing THF between (a) complex (1a) and excess Ph$_2$PCH$_2$CH$_2$SiMe$_2$H (4 h) in the presence of NEt$_3$ and (b) complex (6) and excess Ph$_2$PCH$_2$CH$_2$SiMe$_2$H (12 h). It was identified on the basis of the IR spectrum and $^1$H and $^{31}$P NMR data, all of which were found to be identical with those of an authentic sample.

(8)

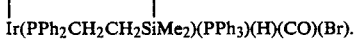

After complex (1a) was stirred with excess NaBr in acetone solution for 15 h, the solvent was removed; the remaining solid was then dissolved in the minimum of THF, and the resulting colorless solution was washed down a short column packed with alumina. Addition of hexane to the eluent precipitated the product (8) as a cream-colored powder. Anal. Calcd for C$_{35}$H$_{36}$BrIrOP$_2$Si: C, 50.35; H, 4.35. Found: C, 50.69; H, 4.30.

(9)

Complex (1a) (0.15 g, 0.19 mmol) in THF (10 mL) was treated with a slight excess of MeMgI in the same solvent (10 mL). After 15 min, the reaction mixture was a very pale yellow color with a trace of solid present. After 10 h a white precipitate had separated leaving a yellow supernatant. Filtration through alumina followed by addition of hexane (10 mL) afforded a yellow solid, which was washed with hexane and then recrystallized (THF/hexane) to give the pure product (a). Anal. Calcd for C$_{35}$H$_{36}$IIrOP$_2$Si: C, 47.67; H, 4.11; I, 14,39. Found: C, 47.48; H, 4.23; I, 14.10.

SYNTHESIS OF PHOSPHINOETHYLSILYL COMPLEXES

A. Five-coordinate compounds
(A1)

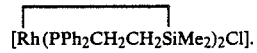

To a stirred solution in THF (10 mL) of [Rh(COD)Cl]$_2$ (0.020 g, 0.41 mmol) was added a solution of PPh$_2$(CH$_2$)$_2$SiMe$_2$H (0.45 g, 1.70 mmol) also in THF (5 mL). After gas evolution had ceased the reaction mixture was stirred (30 min) then volatiles were removed by evacuation of 10$^{-2}$ mm Hg to leave a bright yellow oil. On addition of Et$_2$O (2 mL) the product (A1) (0.45 g, 0.66 mmol, 81%) deposited as translucent yellow crystals. Anal. Calcd. for C$_{32}$H$_{40}$-ClP$_2$RhSi$_2$: C, 56.42; H, 5.91; Cl, 5.20. Found: C, 56.05; H, 5.86; Cl, 5.96%.

(A2)

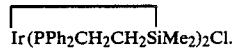

Addition of Ph$_2$P(CH$_2$)$_2$SiMe$_2$H (0.32 g, 1.20 mmol) in THF (5 mL) to a stirred solution of [Ir(COD)Cl]$_2$ (0.20 g, 0.30 mmol) also in THF (10 mL) resulted in gas evolution accompanied by a color-change from red to yellow. After stirring (30 min), the yellow mixture was filtered (alumina column, 5×3 cm$^2$) then solvent was pumped away affording an orange oil. Addition of Et$_2$O (1 mL) gave chrome-yellow crystals of the product (A2) (0.33 g, 0.21 mmol, 35%). Anal. Calcd. for C$_{32}$H$_{40}$OClIrP$_2$Si$_2$: C, 49.88; H, 5.23. Found: C, 50.20; H, 5.55%.

(A3)

After stirring (24 h) complex (A1) (50 mg, 0.07 mmol) with excess NaBr in acetone (20 mL), removal of solvent was followed by extraction with benzene (20 mL). Filtration of the resulting solution, then evaporation of benzene afforded an oily residue which was dissolved in Et$_2$O (1 mL); addition of hexane precipitated the product (A3), ca 90%, as a pale yellow powder. Anal. Calcd. for C$_{32}$H$_{40}$BrP$_2$RhSi$_2$: C, 52.97; H, 51.56. Found: C, 5.61, H, 5.50%.

(A4)

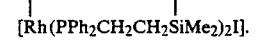

A procedure similar to that described above using NaI in acetone led to isolation of the yellow product (A4), ca 90% yield. Anal. Calcd. for $C_{322}H_{40}IP_2RhSi_2$: C, 49.75; H, 5.22. Found C, 49.84; H, 5.39%.

(A5)

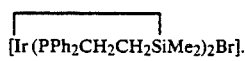
[Ir(PPh₂CH₂CH₂SiMe₂)₂Br].

Compound (A2) (50 mg, 0.06 mmol) was stirred in acetone (20 mL) with excess NaBr for 24 h then solvent was removed to leave a whitish residue. Extraction by stirring (30 min) with benzene (30 mL) followed by filtration and concentration precipitated the yellow product (A5) in essentially quantitative yield. Anal. Calcd. for $C_{32}H_{40}BrIrP_2Si_2$: C, 47.16; H, 4.95. Found: C, 46.97; H, 4.95%.

(A6)

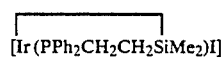
[Ir(PPh₂CH₂CH₂SiMe₂)I]

In a similar manner to that described above, treatment of compound (A2) with NaI in acetone yielded the product (A6) as a yellow powder. Anal. Calcd. for $C_{32}H_{40}IIrP_2Su_2$: C, 44.59; H, 4.68. Found: C, 44.73; H, 4.83%.

(B) Six-coordinate Compounds (B7)

[Ir(PPh₂CH₂CH₂SiMe₂)(COD)(H)(Cl)].

Drop by drop addition of a solution of Ph₂P(CH₂)₂SiMe₂H (0.08 g, 0.30 mmol) in THF (5 mL) to a stirred solution in THF (10 mL) of [Ir(COD)Cl]₂ (0.10 g, 0.15 mmol) rapidly discharged the red color of the latter and after 5 min removal of solvent (B7) left a pale yellow oil. Addition of Et₂O (1 mL) gave the product (0.12 g, 0.20 mmol, 67%) as ivory crystals. Anal. Calcd. for $C_{24}H_{33}ClIrPSi$: C, 47.319; H, 5.47; Cl, 5.83. Found: C, 47.53; H. 5.33; Cl, 6.27%.

(B8)

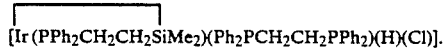
[Ir(PPh₂CH₂CH₂SiMe₂)(Ph₂PCH₂CH₂PPh₂)(H)(Cl)].

Diphos(bisdiphenylphosphinoethane (32 mg, 0.08 mmol) dissolved in THF (10 mL) was added dropwise to a stirred solution of complex (B7) (50 mg, 0.08 mmol) in THF (10 mL). After 5 min the mixture was filtered through an alumina plug (5×3 cm²); removal of solvent gave a yellow oil which was redissolved in the minimum Et₂O then hexane was added precipitating the pale yellow powdery product (B8) (35 mg, 0.04 mmol, 50%). Anal Calcd. for $C_{42}H_{45}ClIrP_3Si$: C, 56.14; H, 5.05. Found: C, 55,98; H, 5.40%.

(B9)

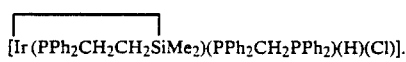
[Ir(PPh₂CH₂CH₂SiMe₂)(PPh₂CH₂PPh₂)(H)(Cl)].

Addition of dpm (bisdiphenylphosphinomethane: 30 mg, 0.08 mmol) in THF (5 mL) to a solution in THF (10 mL) of complex 7 (50 mg, 0.08 mmol) followed by stirring (5 min) then removal of solvent afforded a yellow oil. Redisollution in Et₂O (2 mL) then addition of hexane (15 mL) precipitated the pale yellow product (B9) (59 mg, 0.07 mmol, 83%). Anal. Calcd. for $C_{41}C_{43}ClIrP_3Si$: C, 55,68; H, 4.90. Found: C, 56.29; H, 5.34%.

(C) Six-coordinate Adducts of Complexes (A1) and (A2)

(C10)

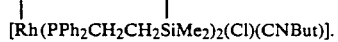
[Rh(PPh₂CH₂CH₂SiMe₂)₂(Cl)(CNBu$^t$)].

On adding Bu$^t$NC (ca 6 mg, 0.07 mmol) in THF (1 mL) to a solution of compound (A1) (50 mg, 0.07 mmol) in THF (2 mL) an immediate lightening in color was observed and removal of volatiles followed by addition Et₂O (1 mL) yielded the cream microcrystalline product (C10) (51 mg, 0.066 mmol, 91%). Anal. Calcd. for $C_{37}H_{49}ClNP_2RhSi_2$: C, 58.15; H, 6.46; N, 1.83. Found: C, 57.28; H, 5.72; N, 1.79%.

(C11 and C12)

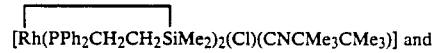
[Rh(PPh₂CH₂CH₂SiMe₂)₂(Cl)(CNCMe₃CMe₃)] and

[Rh(PPh₂CH₂CH₂SiMe₂)₂(Cl)(CNCHMe₂)].

In parallel reactions to that used to obtain compound (C10), complex (A1) was treated with Me₃CCH₂CMe₂NC or Me₂CHNC to give cream-colored, crystalline products in 89, 86% yield respectively. Anal. Calcd. for $C_{41}H_{57}ClNP_2RhSi_2$: C, 60.03; H, 7.00; N, 1.71. Found: C, 59.94; H, 7.33; N, 1.71. Calcd. for $C_{36}G_{47}ClNP_2RhSi_2$: C, 57.63; H, 6.32; N, 1.87. Found: C, 57.58; H, 6.52; N, 1.84%.

(C13)

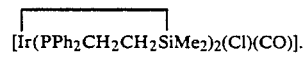
[Ir(PPh₂CH₂CH₂SiMe₂)₂(Cl)(CO)].

Carbon monoxide gas was bubbled through a solution of compound (A2) (50 mg, 0.06 mmol) in THF (5 mL) for 5 min during which time the initially bright yellow color was discharged. Addition of hexane (10 mL) to the resulting clear solution then concentration afforded the product (C13) (46 mg. 0.057 mmol, 88%) as a white powder. Anal. Calcd. for $C_{33}H_{40}ClIrOP_2Si_2$: C, 49.63; H, 5.05. Found: C, 49.77; H, 5.46%.

(C14)

[IrPPh₂CH₂CH₂SiMe₂)₂(Cl)(PF₃)].

Bubbling PF₃ into a solution of complex (A2) (50 mg, 0.06 mmol) in THF (5 mL) led to rapid decolorization and after 5 min the reaction mixture was treated in a manner similar to that described above to give the product (C14) (45 mg, 0.053 mmol, 81%) as a white solid. Anal. Calcd. for $C_{32}H_{40}ClF_3IrP_3Si_2$: Cm, 44.77; H, 4.70. Found: C, 44.75; H, 5.08%.

(C15)

Dropwise addition of a solution of P(OMe)$_3$ (8 mg, 0.06 mmol) in THF (1 mL) to a stirred solution of complex (A2) (50 mg, 0.06 mmol) also in THF (5 mL) resulted in immediate decolorization. Removal of solvent in vacuo, then addition to the residual oil of Et$_2$O (1 mL) afforded colorless crystals of the product (45 mg, 0.05 mmol, 78%). Anal. Calcd. for C$_{35}$H$_{49}$ClIrO$_3$P$_3$Si$_2$: C, 46.99; H, 5.52. Found: C, 47.45; H, 5.46%.

(C16)

This adduct was isolated as a colorless, crystalline product (81% yield) by a method identical to that described for the trimethylphosphite analogue (C15). Anal. Calcd. for C$_{38}$H$_{55}$ClIrO$_3$P$_3$Si$_2$: C, 48.73; H, 5.92. Found: C, 48.45; H, 5.93%.

(C17)

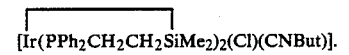

Complex (A2) (50 mg, 0.06 mmol) was dissolved in THF (6 mL) and Bu$^t$NC (6 mg, 0.06 mmol) was added drop-by-drop with stirring. After 5 min solvent was removed from the colorless mixture leaving an oil to which was added Et$_2$O (1 mL). The product (53 mg, 0.62 mmol, 95%) was obtained as colorless crystals. Anal. Calcd. for C$_{37}$H$_{49}$ClIrNP$_2$Si$_2$: C, 52.06; H, 5.79; N, 1.64. Found: C, 51.23; H, 5.61; N, 1.60%.

(C18 and (19)

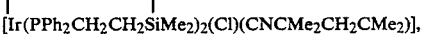

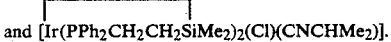

These compounds were prepared by a similar procedure to that described above for complex (C17), by using Me$_3$CCH$_2$CMe$_2$NC or Me$_2$CHNC respectively. Yields of the colorless crystalline products were essentially quantitative. Anal. Calcd. for C$_{41}$H$_{57}$ClIrNP$_2$Si$_2$: C, 54.13; H, 6.32; N, 1.53. Found: C, 54.09; H, 6.39; N, 1.53. Calcd. for C$_{36}$H$_{47}$ClIrNP$_2$Si$_2$: N, 1.53. Found: C, 54.09; H, 6,39; N, 1.53. Calcd. for C$_{36}$H$_{47}$ClIrNP$_2$Si$_2$: C, 51.50; H, 5.64; N, 1.67. Found; C, 50.37; H, 5.42; N, 1.60%.

(D) Related Six-coordinate Ir(III) Complexes
(D20)

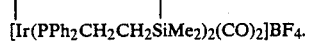

Under an atmosphere of CO gas a solution of AgBF$_4$ (13 mg, 0.07 mmol) in acetone (5 mL) was added to a stirred solution of complex (A2) (50 mg, 0.06 mmol), also in acetone (10 mL). After 30 min the cloudy brown reaction-mixture was filtered through a 5×3 cm$^2$ column packed with CELITE, then solvent was removed leaving an oily residue which dissolved in the minimum of CH$_2$Cl$_2$. On addition of hexane the product (D20) (42 mg, 0.47 mmol, 73%) was precipitated as a white powder. Anal. Calcd. for C$_{34}$H$_{40}$BF$_4$IrO$_2$P$_2$Si$_2$: C, 46.52; H, 4.59. Found: C, 45.42; H, 4.14%.

(D21)

Method A

A suspension of the complex (C13) (52 mg, 0.065 mmol) in 100% EtOH (15 mL) was stirred for 24 h after addition of excess NaBH$_4$ in a further 10 mL EtOH. Replacement of EtOH by benzene (25 mL) was followed by stirring (30 min). Subsequent filtration and slow removal of solvent precipitated the product (D21) (37 mg, 0.48 mmol, 74%) as a cream-colored powder. Anal. Calcd. for C$_{33}$H$_{41}$IrOP$_2$Si$_2$: C, 51.88; H, 5.41. Found: C, 51.92; H, 5.54%.

Method B

To a stirred suspension of compound (A2) (50 mg, 0.06 mmol) in 100% EtOH (10 mL) was added excess NaBH$_4$ in 5 mL EtOH. After 60 min the EtOH was removed, THF (10 mL) was added, and the resulting mixture was filtered to give a pale brown solution into which was bubbled CO gas (5 min). Recovery from Et$_2$O/hexane afforded a product identical (IR, NMR) to that obtained using Method A.

(D22)

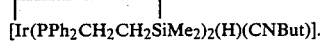

Compound (A2) was dissolved in THF (5 mL) and excess LiAlH$_4$ in THF (1 mL) was added with stirring. After 5 min introduction of excess Bu$^t$NC was followed by stirring for a further 20 h. Filtration through a plug of alumina then removal of solvent in vacuo gave a grayish residue which was extracted into Et$_2$O (1 mL). Slow addition of hexane precipitated the white, powdery product (36 mg, 0.044 mmol, 67%). Anal. Calcd. for C$_{37}$H$_{50}$IrNP$_2$Si$_2$: C, 54.25; H, 6.15; N, 1.71. Found: C, 53.75; H, 6.07; N, 1.91%.

(E) Silyl-Iridium Complex (E1) A chelate-stabilized silyl-iridium(I) complex was formed via reductive elimination from Ir(III) as follows:

UV irradiation was without effect on the cis-dihydridoiridium(III) complex (3)

In fact, prolonged photolysis (250 h, 450-W medium-pressure Hg lamp) in an evacuated quartz tube of a THF solution of compound 3, which results in extensive decomposition, is accompanied by conversion in low yield (<30%) to a product for which IR and $^{31}$P NMR data[12] were compatible with formulation as an irridium(I) species

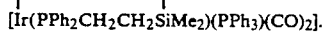

Accordingly a similar reaction performed under an atmosphere of CO gas afforded compound 4 in over 80% yield in only 8 h. The same complex is recovered in ca. 80% yield after filtration and extraction into hexane following treatment of the precursor

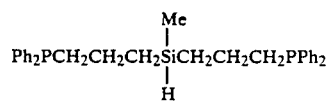

in THF solution with MeMgCl then CO gas. Careful recrystallization (ether/hexane mixture) provided colorless needless of compound 4 suitable for X-ray diffraction. The crystal structure determination confirms the geometry proposed on the basis of the spectral data (ORTEP drawing),

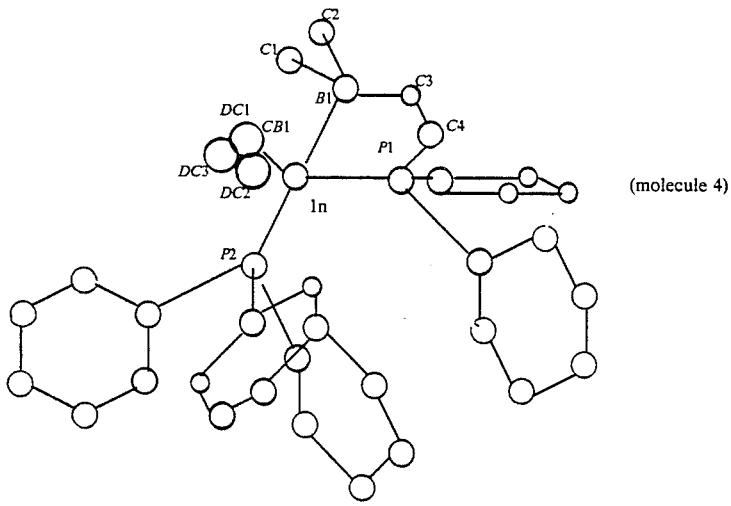

(molecule 4)

Selected bond distances and angles: Ir-Si, 2.454 (6); Ir-P(1), 2.342 (5); Ir-P(2), 2.371 (5); Ir-CO(1), 1.873 (19); Ir-CO (2), 1.795 (24) A. Si-Ir-P(1), 81.9 (2)°; Si-Ir-P(2), 175.7(2)°; P(1)-Ir-P(2), 101.7 (2)°; Si-Ir-CO(1), 87.5 (8)°; Si-Ir-CO(2), 84.1 (8)°; P(1)-Ir-CO(1), 108.2 (7)°; P(1)-Ir-CO(2), 119.6 (6)°; P(2)-Ir-CO(1), 93.5 (8)°; P(2)-Ir-Co(2), 92.0 (8)°.

Examples 1–16 below describe the synthesis of bis- and tris-(phosphenoalkyl)silanes as ligand precursors as the key to formation of the novel complexes which in turn are precursors in platinum chemistry for a novel series of catalytically-useful compounds.

The phosphinoalkylsilanes prepared were all synthesized and purified in a very similar fashion. The appropriate secondary phosphine $R_2PH$ (R=Ph, Cy) was reacted with the desired unsaturated silane giving photo-induced, free radical anti-Markovnikov addition of P-H across the unsaturated bond. Generally an excess of phosphine was used with a variety of solvents. The reagents were placed in a PYREX (trademark) vessel fitted with a high vacuum valve and generally freeze-/thawed three times in liquid nitrogen. The reagents were then photolized using a 450 watt medium pressure mercury 5 to 25 cm from the lamp. Reaction times varied from two days to three months. Purification generally consisted of removal of solvent, if any, in vacuo followed by short path cold cup distillation of the residual secondary phosphine. This was usually achieved at 110° C. and $10^{-2}$ torr. The products were, in all cases except one, clear colourless, very viscous liquids. Products were characterized by $^1H$, $^{13}C$, and $^{31}P$ NMR, infra red, mass spec, and C,H analysis.

EXAMPLE 1

4-methyl-1,7-bis(diphenylphosphino)-4-silaheptane, a bis(phosphinoalkyl)silane (1)

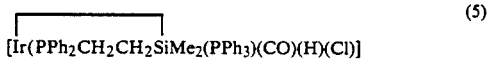

Diphenylphosphine, $PPh_2H$, (3.58 g, 0.0192 mol) was syringed into a greaseless quartz tube. Diallylmethylsilane (1.21 g; 0.00958 mol) was then added with 10 mg of AIBN (azoisisobutyrl-nitrile). The reaction mixture was freeze-thawed three times and then irradiated at a distance of 5 cm from a medium pressure Mercury lamp for 100 hours. The reaction tube was air-cooled during the irradiation, preventing the temperature from rising above 40° C. The resulting product was a viscous, colourless liquid which had to be dissolved in THF to facilitate removal from the quartz tube. Removal of the solvent under vacuum was followed by cold cup distillation for 4 hours at 120° C. and $10^{-2}$ mm Hg to remove the excess $HPPh_2$. The product was obtained in approximately 100% yield based on diallymethylsilane and was characterized by $^1H$, $^{13}C$ (Table 1), $^{31}P$ NMR spectroscopy, by I.R. and mass spectra, and elemental analysis. Anal. Calcd: C, 74.76; H 7.1. Found: C, 74.74; H, 7.16.

EXAMPLE 2

5-methyl-1,9-bis(diphenylphosphino)-5-silanoane (2)

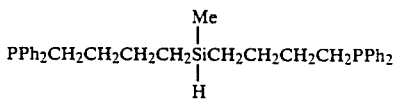

The silane precursor $(MeSi(H)(CH_2CH_2CH=CH_2)_2)$ was synthesized by standard Grignard methods starting from methyldichlorosilane and 4-bromobut-1-ene. This compound was photolyzed with diphenylphosphine PPh$_2$H (3 mol equiv) in a fashion identical to that described in Example 1. The clear colorless viscous product was dissolved in methylene chloride (5 mL) to facilitate removal from the photolysis vessel. The CH$_2$Cl$_2$ and excess PPh$_2$H were removed as described above to yield the pure liquid product which was characterized by NMR spectroscopy and analysis.

EXAMPLE 3

3-methyl-1,5-bis(diphenylphosphino)-3-silapentane (3)

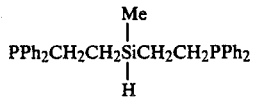

Methyldivinylsilane is required for this synthesis: this known silane was obtained by Grignard methods from vinyl bromide CH$_2$=CHBr and methyldichlorosilane. Following a procedure identical with that described in Examples 1 and 2 involving photolysis with PPh$_2$H, the clear liquid product was prepared and purified.

EXAMPLE 4

1,5-bis-(dicyclohexylphosphino)-3-methyl-3-silapentane (4)

Divinylmethylsilane (approximately $8 \times 10^{-3}$ mol in THF/ether) and dicyclo-hexylphosphine (5.0 mL; 4.5 g; 0.023 mol) were irradiated approximately 25 cm from the UV lamp for 90 days. Removal of the solvent and dicyclohexylphosphine yielded 2.5 g of the colourless product.

EXAMPLE 5

1,5-bis(diphenylphosphino)-3-phenyl-3-silapentane (5)

Divinylphenylsilane (1.6 mL; 1.43 g; $8.94 \times 10^{-3}$ mol) was placed in a PYREX tube and ether (2 mL) added. Diphenylphosphine [Ph$_2$PH] (3.26 mL; 3.49 g; $1.88 \times 10^{-2}$ mol) was added and the sample irradiated approximately 25 cm from the UV lamp for 72 hours. Removal of solvent and diphenylphosphine yielded 4.68 g of a clear colourless, very viscous, liquid. Yield = 98.3%.

EXAMPLE 6

1-(diphenylphosphino)-3-phenyl-3-silapent-4-ene (6)

Ph$_2$PCH$_2$CH$_2$Si(Ph)HCH=CH$_2$

Divinylphenylsilane (1.789 g; $1.12 \times 10^{-2}$ mol) and ether (20 mL) was placed in a PYREX tube with diphenylphosphine (1.96 mL; 2.10 g; $1.12 \times 10^{-2}$ mol). The solution was irradiated for 50 hours approximately 25 cm from the UV lamp. Vacuum distillation at approximately $10^{-2}$ torr yielded unreacted divinylphenylsilane at 80° C. and the desired product at 200° C. 1.04 g of a clear, colourless liquid was obtained. Yield = 27.5%.

EXAMPLE 7

1-(Dicyclohexylphosphino)-5-(diphenylphosphino)-3-phenyl-silapentane (7)

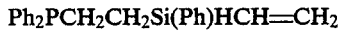

1-(diphenylphosphino)-3-phenyl-3-silapent-4-ene (1.0 g; $2.95 \times 10^{-3}$ mol) was placed in a PYREX tube and ether (2 mL) and dicyclohexyphosphine (0.61 g; $3.24 \times 10^{-3}$ mol) added. The solution was irradiated for 200 hours. Removal of solvent and unreacted starting materials yielded 1.45 g of a clear, colourless product. Yield = 93.5%.

EXAMPLE 8

1,5-bis(dicyclohexylphosphino)-3-phenyl-3-silapentane (8)

Cy$_2$CH$_2$CH$_2$Si(Ph)HCH$_2$CH$_2$PCy$_2$

Divinylphenylsilane (1.5 mL; 1.34 g; $8.38 \times 10^{-3}$ mol), ether (2 mL) and dicylohexylphosphine (4 mL; 3.62 g; $1.82 \times 10^{-2}$ mol) were irradiated for 100 hours approximately 25 cm from the UV lamp. Removal of solvent and dicyclohexylphosphine yielded 4.35 g of a clear colourless, very viscous liquid. Yield = 93.1%.

EXAMPLE 9 tri(-2-diphenylphosphinoethyl)silane (9)

(Ph$_2$PCH$_2$CH$_2$)$_3$SiH

Trivinylsilane (approximately 0.4 g in 4 mL THF/ether) and diphenylphosphine (2.0 mL; 2.14 g; $1.11 \times 1^{-2}$ mol) was irradiated for 70 hours approximately 25 cm from the UV lamp. Removal of the solvent and diphenylphosphine yielded 2.2 g of product. The product was initially obtained as a liquid, but upon manipulation formed a sticky white solid.

EXAMPLE 10 tris(-2-dicyclohexylphosphinoethyl)silane (10)

Cy$_2$PCH$_2$CH$_2$)$_3$SiH

Trivinylsilane (approximately 0.5 g in 20 mL THF/ether) and dicyclohexylphosphine (4.0 mL; 3.57 g; $1.80 \times 10^{-2}$ mol) was irradiated for 1440 hours approximately 25 cm from the UV lamp. Removal of the solvent and excess dicyclohexylphosphine yielded 2.5 g of a slightly yellow, very sticky liquid.

EXAMPLE 11

1,7-bis(dicyclohexylphosphino)-4-methyl-4-silaheptane (11)

Cy$_2$PCH$_2$CH$_2$CH$_2$Si(CH$_3$)HCH$_2$CH$_2$CH$_2$PCy$_2$

Diallylmethylsilane (1.0 mL; 0.77 g; $6.02 \times 10^{-3}$ mol) and dicyclohexylphosphine (2.8 mL; 2.54 g; $1.28 \times 10^{-2}$ mol) was irradiated in a PYREX tube for 300 hours approximately 6 cm from the UV lamp with air cooling on the sample tube. Removal of dicyclohexylphosphine yielded 2.86 g of a clear, colourless, very viscous liquid. Yield = 91.2%.

EXAMPLE 12

1-(diphenylphosphino)-4-methyl-4-silahept-6-ene (12)

Ph$_2$PCH$_2$CH$_2$CH$_2$Si(CH$_3$)HCH$_2$CH=CH$_2$

Diallylmethylsilane (1.008 g; $7.98 \times 10^{-3}$ mol), ether (10 mL) and diphenylphosphine (1.40 mL; 1.50 g; $7.98 \times 10^{-3}$ mol) was irradiated approximately 25 cm from the UV lamp for 400 hours. The product was obtained via short path vacuum distillation at 220° C. and $10^{-2}$ torr. 0.5 g of a clear, colourless liquid was obtained. Yield = 19.9%.

EXAMPLE 13

1-(dicyclohexylphosphino)-7-(diphenylphosphino)-4-methyl-4-silaheptane (13)

Cy$_2$PCH$_2$CH$_2$CH$_2$Si(CH$_3$)HCH$_2$CH$_2$CH$_2$PPh$_2$ 1-(diphenylphosphino)-4-methyl-4-silahept-6-ene (0.45 g; 1.43×10$^{-3}$ mol), benzene (7 mL) and dicyclohexylphosphine (0.70 g; 3.5×10$^{-3}$ mol) was irradiated for 3000 hours.

EXAMPLE 14

1,7-bis(diphenylphosphino)-4-phenyl-4-silaheptane (14)

Ph$_2$PCH$_2$CH$_2$CH$_2$Si(Ph)HCH$_2$CH$_2$CH$_2$PPh$_2$

Diallylphenylsilane (1.50 mL; 1.316 g; 6.987×10$^{-3}$ mol), ether (2 mL) and diphenylphosphine (3.0 ml; 3.25 g; 1.75×10$^{-2}$ mol) was irradiated approximately 25 cm from the UV lamp for 360 hours. Removal of solvent and diphenylphosphine yielded 3.28 g of a clear, colourless, very viscous liquid. Yield=83.7%.

EXAMPLE 15

1,7-bis(dicyclohexylphosphino)-4-phenyl-4-silaheptane (15)

Cy$_2$PCH$_2$CH$_2$CH$_2$Si(Ph)HCH$_2$CH$_2$CH$_2$PCy$_2$

Diallylphenylsilane (0.854 g; 4.53×10$^{-3}$ mol) and dicyclohexylphosphine (2.10 ml; 1.89 g; 9.52×10$^{-3}$ mol) were placed in a quartz tube and irradiated approximately 25 cm from the UV lamp for 1000 hours. During the reaction the solution darkened and some brown solid formed. Filtration and removal of the dicyclohexylphosphine resulted in a mixture consisting mostly of the product, but containing impurities which could not be removed.

EXAMPLE 16 tris(-3-diphenylphosphinopropyl)silane (16)

(Ph$_2$PCH$_2$CH$_2$CH$_2$)$_3$SiH

Triallylsilane (1.02 g;p 6.66×10$^{-3}$ mol), hexanes (10 mL) and diphenylphosphine (4.7 mL; 5.02 g; 2.66×10$^{-2}$ mol) were placed in a PYREX tube and irradiated for 360 hours approximately 25 cm from the UV lamp. Removal of solvent and diphenylphosphine yielded 4.2 g of a cloudy, white, very viscous liquid. Yield=87.9%.

Examples 17 and 18 describe the synthesis of representative bis(phosphinoalkyl)silyl complexes of Rh(III) and Ir(III).

EXAMPLE 17

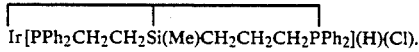
Ir[PPh$_2$CH$_2$CH$_2$Si(Me)CH$_2$CH$_2$CH$_2$PPh$_2$](H)(Cl).

The bis(phosphinopropyl)silane prepared as described in Example 1 (0.188 g, 0.38 mmol) was weighed. Cloro(cyclo-octa-1,5-diene)iridium dimer, (IR(COD)Cl)$_2$ (0.1265 g; 0.1883 mmol) was weighed into a Schlenk tube which was subsequently evacuated then purged with N$_2$ gas, and dissolved in THF (15 ml). The bis(phosphinoalkyl)silane solution was added to the stirring orange solution in THF (2×5 mol) causing an immediate lightening to a yellow color. The resultant solution was stirred for 5½ hours and pumped on overnight yielding a yellow solid which was scraped to give a powder. Green-yellow crystals were obtained from an ether/hexane mixture in the freezer. $^1$H, $^{13}$C, $^{31}$P NMR spectroscopy, by I.R. spectroscopy and elemental analysis. Anal. Calcd: C, 51.26; H, 4.99. Found: C, 51.46; H, 4.99.

EXAMPLE 17A

Structural Characterization of the bis(phosphinoalkyl)silyl-iridium(III) complex obtained as described in Example 17

Crystals of the complex suitable for single-crystal X-ray diffraction were grown from cold ether/hexane solutions. Crystal data: M$_1$=726.3; space group P$_{21}$/n; Å, a=11.0387 (10) Å, b 24.3222 (12) Å, c=11.3177 (10); V (A3)=3010.56 (10); Z=4; D$_{calcd}$=1.60 g cm$^3$; MoK α radiation=44.91 radiation, μ=0.71069 cm$^{-1}$; 3268 observed reflections refined to a conventional R=0.0375 (R$_w$=0.0449).

EXAMPLE 18

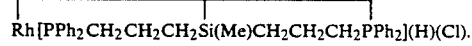
Rh[PPh$_2$CH$_2$CH$_2$CH$_2$Si(Me)CH$_2$CH$_2$CH$_2$PPh$_2$](H)(Cl).

Following a procedure similar to that described in Example 4 using chloro(cycloocta-1,5-diene)rhodium dimer as the organometallic precursor, the rhodium (III) analogue of the iridium(III) structurally characterized (Example 5) was prepared and identified by $^1$H and $^{31}$P NMR spectroscopy and IR spectroscopy.

Examples 19-27 describe the synthesis of representative bis(phosphinoalkyl)silyl complexes of Pt(II).

Metal complexes were synthesized by the reaction of stoichiometric quantity of the respective ligand precursor with a suitable metal complex. The metal reagents were synthesized according to literature methods. Due to the very viscous and air-sensitive nature of the ligand precursors, special techniques were employed to weigh small accurate quantities. Typically, a glass weighing bottle fitted with a ground glass joint and containing a small glass "spoon" was placed in a wide mouth Schlenk tube (B 34), evacuated and let down to an N$_2$ atmosphere. The stopper was then inserted and the weighing bottle weighed. The weighing bottle was then placed in the Schlenk tube, and the glass "spoon" removed with a pair of long forceps. The "spoon" was then dipped in the viscous ligand precursor to collect some of the material. After rapid transfer of the spoon back to the weighing bottle, the sample was evacuated, let down to an N$_2$ atmosphere, and weighted. One such transfer would generally consist of approximately 50 mg of compound. More compound could be obtained by repeated transfers or by the use of more than one "spoon". The above technique can be used to obtain small quantities of viscous, air-sensitive materials of an accurate weight. Once the mass of the ligand precursor was known, the stoichiometric amount of the reagent metal complex was calculated and weighed out. This was then placed in a Schlenk tube, evacuated, let down to an N$_2$ atmosphere, and dissolved in the solvent of choice. The ligand precursor, in the glass weighing bottle, was then dissolved in the same solvent and transferred to the stirring solution of the metal complex. The reaction mixture was then stirred for varying lengths of time after which the solvent was removed in vacuo. A variety of purification techniques were then employed depending on the sample in question.

EXAMPLE 19

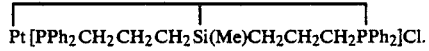
Pt[PPh$_2$CH$_2$CH$_2$CH$_2$Si(Me)CH$_2$CH$_2$CH$_2$PPh$_2$]Cl.

This bis(phosphinopropyl)silane obtained by the procedure described in Example 1 (0.2426 g; 0.487 mmol) was transferred from a weighing bottle under N$_2$ into a Schlenk tube with the addition of benzene (4×5 mL). Distilled NEt$_3$ (2.4 mL; 0.016 mol) was added to this solution. Dichloro(cycloocta-1,5-diene)platinum (II), (COD)PtCl$_2$ (0.1825 g; 0.0487 mmol) was placed in a Schlenk tube with benzene (15 mL). The white solid did not dissolve. The ligand/NEt$_3$ solution was added to the stirring (COD)PtCl$_2$ suspension over 20 seconds causing a yellowing and the formation of a very fine precipitate. The solvent was pumped off after 15 min yielding a bubbly yellow oil/solid. Benzene (30 mL) was added and the resulting yellow solution was filtered through 5 mm of FLORISIL on a glass frit. Pumping away of volatiles left a solid reside which was washed with hexane (2×5 mL) to yield pure product in greater than 95% yield. The product was characterized by $^1$H, $^{13}$C, $^{31}$P an d$^{195}$Pt NMR spectroscopy, by I.R. and by mass spectra, and by elemental analysis. Anal. Calcd; C, 51.13; H 4.85. Found: C, 50.99; H, 4.81.

EXAMPLE 19A

Structural Characterization of the bis(phosphinoalkyl)silyl-platinum(II) complex obtained as described in Example 19

Crystals of the complex were obtained from a saturated ether solution. Crystal data: M$_1$=728.2; space group I12/al Å, a=21.5818 (20) Å, b=12.7136 (15) Å, c=22,1190 (20); V (A3)=6050.36 (20); Z=8; D$_{calcd}$=1.58 g cm$^3$; MoK α radiation =48.51; μ=0.71069; 2735 observed reflections refined to a conventional R=0.0876 (R$_2$=0.841).

EXAMPLE 20

Pt[PPh$_2$CH$_2$CH$_2$CH$_2$Si(Me)CH$_2$CH$_2$CH$_2$PPh$_2$]SnCl$_3$.

The product obtained as described in Example 6 (0.073 g; 0.10 mmol) was dissolved in benzene (10 mL). Anhydrous SnCl$_2$ (0.025 g; 0.13 mmol) was added but did not appear to dissolve and the reaction mixture remained colorless. After 15 min THF (2 mL) was added, at which point the SnCl$_2$ dissolved and a fine orange-yellow suspension began to form. Subsequent removal of the solvent mixture afforded an orange product which was characterized by using $^{31}$P NMR spectroscopy.

EXAMPLE 21

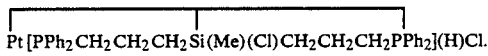
Pt[PPh$_2$CH$_2$CH$_2$CH$_2$Si(Me)(Cl)CH$_2$CH$_2$CH$_2$PPh$_2$](H)Cl.

Addition of benzene saturated with HCl gas (1 mol equiv vs Pt complex) to the product obtained as described in Example 6 also dissolved in benzene resulted in an initial color change to pale yellow followed by formation of a colorless solution. Evaporation of benzene afforded a white solid product which has characterized by NMR and IR spectroscopy.

EXAMPLE 22

{1,5-bis(diphenylphosphino)-3-methyl-3-silylpentane} platinum(II)chloride (22)

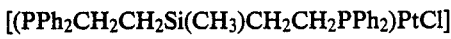
[(PPh$_2$CH$_2$CH$_2$Si(CH$_3$)CH$_2$CH$_2$PPh$_2$)PtCl]

(COD)PtCl$_2$ (0.0786 g; 2.098×10$^{-4}$ mol) and PPh$_2$CH$_2$CH$_2$Si(CH$_3$)HCH$_2$CH$_2$PPh$_2$ (0.0987 g; 2.098×10$^{-4}$ mol) were mixed in THF (2×6 mL) with NEt$_3$ (approximately 1 mL) present. Removal of solvent in vacuo followed by washing with THF (3×5 mL) yielded 0.135 g. of a white solid, insoluble in all solvents investigated. Yield=92.0%.

EXAMPLE 23

{1,5-bis(dicyclohexylphosphino)-3-methyl-3-silylpentane}platinum(II)chloride (23)

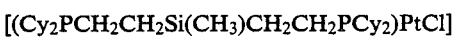
[(Cy$_2$PCH$_2$CH$_2$Si(CH$_3$)CH$_2$CH$_2$PCy$_2$)PtCl]

(COD)PtCl$_2$ (0.1535 g; 4.098×10$^{-4}$ mol) and Cy$_2$PCH$_2$CH$_2$Si(CH$_3$)HCH$_2$CH$_2$PCy$_2$ (0.2027 g; 4.098×10$^{-4}$ mol) were combined in THF (2×10 mL) with NEt$_3$ (approximately 1 mL). Removal of the solvent in vacuo followed by extraction with benzene (3×5 mL) yielded 0.250 g. of a white solid. Yield=84.3%.

EXAMPLE 24

{1,5-bis(dicyclohexylphosphino)-3-phenyl-3-silylpentane}platinum(II)chloride (24)

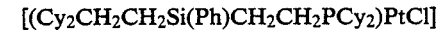
[(Cy$_2$CH$_2$CH$_2$Si(Ph)CH$_2$CH$_2$PCy$_2$)PtCl]

(COD)PtCl$_2$ (0.104 g; 2.77×10$^{-3}$ mol) and Cy$_2$PCH$_2$CH$_2$Si(Ph)CH$_2$CH$_2$PCy$_2$ (0.154 g; 2.77×10$^{-4}$ mol) were combined in benzene (2×10 mL) with NeT$_3$ (approximately 1 mL). Removal of the solvent in vacuo followed by extraction with benzene (2×10 mL) yielded 0.075 g. of a white solid. Yield=34.5%.

EXAMPLE 25

{1-(dicyclohexylphosphino)-5-(diphenylphosphino)-3-phenyl-3-silylpentane}platinum(II)chloride (25)

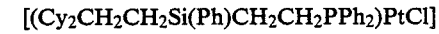
[(Cy$_2$CH$_2$CH$_2$Si(Ph)CH$_2$CH$_2$PPh$_2$)PtCl]

(COD)PtCl$_2$ (0.0782 g; 2.09×10$^{-4}$ mol) and Cy$_2$PCH$_2$CH$_2$Si(Ph)HCH$_2$CH$_2$PPh$_2$ (0.114 g; 2.09×10$^{-4}$ mol) were combined in benzene (2×10 mL) with NEt$_3$ (approximately 1 mL). Removal of the solvent in vacuo yielded 0.1220 g. of an off-white solid. Yield=75.4%

EXAMPLE 26

{1,7-bis(diphenylphosphino)-4-phenyl-4-silylpentane} platinum(II)chloride (26)

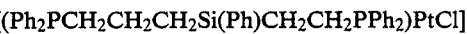
[(Ph$_2$PCH$_2$CH$_2$CH$_2$Si(Ph)CH$_2$CH$_2$PPh$_2$)PtCl]

(COD)PtCl$_2$ (0.199 g; 5.33×10$^{-4}$ mol) and Ph$_2$PCH$_2$CH$_2$CH$_2$CH$_2$Si(Ph)HCH$_2$CH$_2$PPh$_2$ (0.299 g; 5.33×10$^{-4}$ mol) were combined in benzene (2×10 mL) with NEt$_3$ (approximately 1 mL). Removal of the solvent in vacuo followed by extraction and filtration with benzene yielded 0.305 g. of a cream coloured solid. Yield=72.4%.

EXAMPLE 27

{1,7-bis(dicyclohexylphosphino)-4-methyl-4-silylheptane}platinum(II)chloride (27)

[(Cy$_2$PCH$_2$CH$_2$CH$_2$Si(CH$_3$)CH$_2$CH$_2$CH$_2$PCy$_2$)PtCl]

(COD)PtCl$_2$ (0.1327 g; 3.541×10$^{-4}$ mol) and Cy$_2$PCH$_2$CH$_2$CH$_2$Si(CH$_3$)CH$_2$CH$_3$CH$_2$PCy$_2$ (0.1851 g; 3.541×10$^{-4}$ mol) were combined in benzene (2×10 mL) with NEt$_3$ (approximately 1 mL). Removal of the solvent in vacuo followed by extraction and filtration with benzene yielded 0.2014 g. of a cream coloured solid. Yield=75.5%.

Examples 28–34 describe the synthesis of representative bis- and tris(phosphinoalkyl)silyl complexes of Rh(I), Rh(III), and Ir(III).

EXAMPLE 28

{1,7-bis(diphenylphosphino)-4-methyl-4-silylheptane}hydridocarbonyliridium(III)chloride (28)

[(PPh$_2$CH$_2$CH$_2$CH$_2$Si(CH$_3$)CH$_2$CH$_2$CH$_2$PPh$_2$)IR(H)(CO)(Cl)]

(PPh$_3$)$_2$Ir(CO)(Cl) (0.5656 g; 7.251×10$^{-4}$ mol) and PPh$_2$CH$_2$CH$_2$CH$_2$Si(CH$_3$)HCH$_2$CH$_2$CH$_2$PPh$_2$ (0.3611 g; 7.25×10$^{-4}$ mol) were combined in CH$_2$Cl$_2$ (2×10 mL). The initially yellow suspension gave away to a colourless solution. Removal of the solvent in vacuo yielded a white sticky solid which was washed with ether (3×5 mL). Removal of the residual ether in vacuo yielded 0.361 g of a fine white powder. Yield=66.0%.

EXAMPLE 29

{1,7-bis(diphenylphosphino)-4-methyl-4-silylheptane}hydridotriclorostanyliridium(III)carbonyl (29)

[(PPh$_2$CH$_2$CH$_2$CH$_2$Si(CH$_3$)CH$_2$CH$_2$CH$_2$PPh$_2$)Ir(SnCl$_3$)H(CO)]

I(PPh$_2$)CH$_2$CH$_2$CH$_2$Si(CH$_3$)CH$_2$CH$_2$CH$_2$PPh$_2$)Ir(H)(CO)(Cl)](0.080 g; 1.06×10$^{-4}$ mol) and SnCl$_2$ (0.0201 g; 1.06×10$^{-4}$ mol) were combined in THF (10 mL) and stirred for 1 hour. Removal of solvent in vacuo yielded 0.100 g of a fine white solid. Yield=99.9%.

EXAMPLE 30

{tris(-2-diphenylphosphinoethyl)silyl}iridium(III) hydridochloride (30)

[((PPH$_2$CH$_2$CH$_2$)$_3$Si)IR(H)(Cl)]

[(COD)IrCl]$_2$ (0.1264 g; 3.764×10$^{-4}$ mol) was added to a stirring solution of (PPh$_2$CH$_2$CH$_2$CH$_2$)$_3$SiH (0.2517 g; 3.76×10$^{-4}$ mol) in THF (15 mL). Removal of the solvent in vacuo from the yellow solution yielded 0.3112 g of a brownish solid. Yield=92.2%.

EXAMPLE 31

{1,7-bis(diphenylphosphino)-4-methyl-4-silylheptane}hydridocarbonyliridium(III)chloride (31)

[(PPh$_2$CH$_2$CH$_2$CH$_2$Si(CH)$_3$CH$_2$CH$_2$CH$_2$PPh$_2$)IR(H)(CO)(Cl)]

[(PPh$_2$CH$_2$CH$_2$CH$_2$Si(CH$_3$)HCH$_2$CH$_2$CH$_2$PPh$_2$ (0.0781 g; 1.586×10$^{-4}$ mol) in benzene (5 mL) was added to a stirring suspension of [(PPh$_3$)$_2$Rh(CO)(Cl)](0.1083 g; 1.586×10$^{-4}$ mol) in benzene (3 mL). The solid dissolved immediately upon the above addition yielding a light yellow solution. Removal of the solvent in vacuo yielded 0.095 g of a light yellow solid. Yield=91.2%.

EXAMPLE 32

{tris(-2-diphenylphosphinoethyl)silyl}rhodium(III) hydridochloride (32)

[((PPh$_2$CH$_2$CH$_2$)$_3$Si)Rh(H)(Cl)]

(1) [(COD)Rh(Cl)]$_2$ (0.1439 g; 2.94×10$^{-4}$ mol) was dissolved in THF (10 mL) and a solution of (PPh$_2$CH$_2$CH$_2$)$_3$SiH (0.3912 g; 5.849×10$^{-4}$ mol) in THF (10 mL) added. After approximately 1 min., a flocculent yellow precipitate formed. Removal of the solvent in vacuo yielded 0.4349 g of a yellow/brown solid. Yield=92.1%.

(2) [(PPh$_3$)$_2$Rh(CO)(Cl)](0.1014 g; 1.454×10$^{-4}$ mol) was dissolved in THF (10 mL) and (PPh$_2$CH$_2$CH$_2$)SiH (0.0982 g; 1.464×10$^{-4}$ mol) added in THF (5 mL). Removal of the solvent in vacuo followed by washing with ether (3×5 mL) yielded 0.085 g of a yellow/brown solid. Yield=71.8%.

EXAMPLE 33

{tris(-2-diphenylphosphinoethyl)silyl}rhodium(I)carbonyl (33)

[((PPh$_2$CH$_2$CH$_2$)$_3$Si)Rh(CO)

(1) (PPh$_2$CH$_2$CH$_2$)$_3$SiH (0.106 g; 1.59×10$^{-4}$ mol) and [(PPh$_3$)$_3$Rh(H)(CO)](0.145 g; 1.59×10$^{-4}$ mol) were added together and THF (10 mL) added. Immediate gas evolution was evident (H$_2$). Removal of the solvent in vacuo from the yellow solution, followed by washing with ether (3×5 mL) yielded 0.065 g of a bright yellow micro-crystalline solid. Yield=51.4%.

(2) [((PPh$_2$CH$_2$CH$_2$)$_3$Si)Rh(H)(Cl)](0.2000 g; 2.47×10$^{-4}$ mol) was dissolved in THF (20 mL) and placed under CO at 1 atm. for 5 min. Excess LiAlH$_4$ was added and the grey suspension filtered through an alumina plug. Removal of the solvent in vacuo yielded 0.095 g of a fine yellow solid. Yield=48.0%.

EXAMPLE 34

{tris(-2-diphenylphosphinoethyl)silyl}rhodium(I)carbonyl triphenylphosphine (34)

[((PPh$_2$CH$_2$CH$_2$)$_3$Si)Rh(PPh$_3$)]

(PPh$_2$CH$_2$CH$_2$)$_3$SiH (0.0876 g; 1.23×10$^{-4}$ mol) was dissolved in THF (5 mL) and [PPh$_3$)$_4$Rh(H)] (0.1422 g; 1.234×10$^{-4}$ mol) added. Removal of the solvent in vacuo followed by washing with ether (2×5 mL) yielded 0.075 g of a black/green solid. It was not possible to remove all of the excess triphenylphosphine from the sample. Yield=56.5%.

Examples I, II and III below describe the activity of the complexes described above as hydroformylation catalysts. The procedure was carried out using standardized experimental conditions. A Parr Model 4561 300 mL stainless steel pressure reactor ('bomb') was used in all cases.

The following procedure should be used for screening compounds for hydroformylation catalysts.

1. Bomb conditions should be standardised at 70° C. and 1000 p.s.i. total pressure with a 50:50 mix CO and H$_2$ for 16 hrs. A TEFLON liner should not be used since the temperature fluctuations are too great. A small glass flask should be used and the temperature should be allowed to rise slowly. The bomb must be flushed at least three times with CO before charging it finally. The pressure must be lowered slowly on completion to avoid flash vapourisation.

2. The catalyst-to-substrate (1-hexene) ratio should be kept roughly the same for all runs, $5 \times 10^{-5}$ mole catalyst should be used in 3 mls 1-hexene and 4 mls benzene.

The gases were vented off slowly and the products analysed by GLC and mass spectrometry. The results are summarized below:

| Catalyst | Yield (%) (including hexane) | Selectivity to aldehydes | Ratio straight:branched |
| --- | --- | --- | --- |
| ⌐⎯⎯⎯⎯⎯⎯⎯¬<br>IrPPh$_2$CH$_2$CH$_2$SiMe$_2$(CO)PPh$_3$H$_2$ | 66 | 87.2 | 2.56:1 |
| ⌐⎯⎯⎯⎯⎯⎯⎯¬<br>IrPPh$_2$CH$_2$CH$_2$SiMe$_2$(C$_8$H$_{12}$)H(Cl) | 100 | 27 | 1.16:1 |
| ⌐⎯⎯⎯⎯⎯⎯⎯¬<br>IrPPh$_2$CH$_2$CH$_2$SiMe$_2$(PPh$_2$CH$_2$CH$_2$PPh$_2$)H(Cl) | No catalytic Activity | | |
| ⌐⎯⎯⎯⎯⎯⎯⎯¬<br>IrPPh$_2$CH$_2$CH$_2$SiMe$_2$PPh$_3$(CO)H(Cl) | 18.2 | 73.8 | 2.9:1 |
| ⌐⎯⎯⎯⎯⎯⎯⎯¬<br>IrPPh$_2$CH$_2$CH$_2$SiMe$_2$PPh$_3$(CO)H(Cl) + SnCl$_2$ | 7.03 | 30.9 | 2.9:1 |
| ⌐⎯⎯⎯⎯⎯⎯⎯¬<br>IrPPh$_2$CH$_2$CH$_2$SiMe$_2$(CO)$_2$PPh$_3$ | 22.5 | 74.4 | 2.8:1 |
| ⌐⎯⎯⎯⎯⎯⎯⎯¬<br>RhPPh$_2$(CH$_2$)$_3$SiMe(CH$_2$)$_3$PPh$_2$(H)Cl | 100 | 100 | 1.09:1 |

3. The pressure should be taken at regular intervals since this gives a good indication of the rate. If the pressure drop is very quick then further experiments should be carried out at lower temperature and pressures.

4. Products from the bomb can be characterised by G.C. and G.C./M.S. (if required). Since hydrogenation may take place as well, it is necessary to set the G.C. condition to achieved good separation of hexane from hexene. For A 0.5 ul injection the following conditions will achieve adequate separation.

TEMP. 26° C. for 3 mins. then 15° C./min to 240° C. It may be necessary to adjust the attenuation for satisfactory results. Under these conditions, the hexane and hexene will come off after 2.5 mins with 0.1 min separation (both peaks will have to be on scale); the aldehydes will come off much later (6–8 mins). With these starting materials, the two major aldehydes should be 2-methylhexanal and heptanal, the latter having the longest retention time. Retention times can e checked by adding a small quantity of the pure material to peak enhance the chromatogram.

5. It is important that from time to time the state of the glass liner in the injector port must be checked. If it has any metal deposits at all the glass must be cleaned and replaced. The bomb must be cleaned thoroughly between runs.

DESCRIPTION OF USE OF THE INVENTION

EXAMPLE I

Process for the Catalytic Hydroformylation of Hex-1-ene by Various Phosphinoalkylsilyl Complexes The bomb was charged with 1-hexene (3 mL, 24 mmol), benzene (4 mL, 45 mmol) and catalyst ($5 \times 10^2$ mmol). After repeated flushing with CO, the bomb was pressured to 1000 p.s.i. with a 1:1 mixture of CO/H$_2$. The temperature of the reactor was raised slowly to 70° C. and maintained for 16 hours then allowed to cool.

EXAMPLE II

Process for Catalytic Hydroformylation of Hex-1-ene by Bis(phosphinoalkyl)silyl Complexes of platinum(II)

(a) The product obtained as described in Example 6 shows no detectable catalytic activity (hydrogenation or hydroformylation) under the standard test-condition detailed above.

(b) The product obtained as described in Example 6 (22 mg) with SnCl$_2$ (2 mol equiv., 11.4 mg) was used as catalyst for hex-1-ene hydroformylation under conditions similar to those already specified above. Using hex-1-ene (3 mL) and benzene (4 mL) with CO (400 psi) and H$_2$ (400 psi) with heating to 75° C. for 15 h conversion to C$_7$ aldehydes was 29% with 93% n-heptaldehyde (13.3:1 n:islo).

Repeat runs (3) set up in the same way yielded highly consistent results (93%, 93%, 94% selectivity). At the end of these experiments the solution recovered from the bomb was clear orange becoming cloudy over ca 1 h at ambient.

(c) The product obtained as described in Example 8 (23 mg) with SnCl$_2$ (1 mol equiv., 5.0 mg) was used as catalyst in an experiment set up as in Example 12(b). At the end of the run conversion was 34.7% with 92% selectivity (11.5:1 ratio).

As described above, the activity of a range of complexes as catalysis in the hydroformylation of hex-1-ene to heptaldehydes has been investigated. Typical conditions are 70°–100° C. using total 1000 psi of equimolar CO/H$_2$ mixtures. Product mixtures were analyzed by GLC. Products were identified using GLC retention time, mass spectrometry, and $^1$H NMR spectroscopy.

The significant catalytic properties of the complexes of this invention are as follows:

(1) Olefin hydroformylation is strongly preferred over hydrogenation in most cases: this is a significant observation in view of its commercial desirability.

(2) In terms of rate, most of the complexes show moderate to high activity.

(3) In terms of selectivity the novel complexes of aspects of this invention show very high straight-chain: branched ratios.

The phosphinoalkylsilyl complexes of Rh, Ir, and Pt are catalysts for hydroformylation of hex-1-ene to heptaldehydes. Selectivity vs hydrogenation and overall conversion rates are generally good. Selectivity n vs branched heptaldehyde product is generally high.

The Pt complex

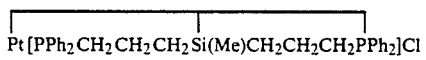

is inactive for hex-1-ene hydroformylation (or hydrogenation) under the conditions tested, but in the presence of stannous chloride $SnCl_2$ as promoter it is efficient hydroformylation catalyst with no evidence for competing hydrogenation and with a very high (ca 20:1) selectivity for n vs branched heptaldehyde.

EXAMPLE III

Process for Catalytic Hydroformylation of Oct-1-ene by Tris(phosphinoalkyl)silyl Complex of rhodium(I)

The product obtained as described in Example 33 above (25.7 mg; $3.22 \times 10^{-5}$ mol) was used as catalyst for oct-1-ene hydroformylation under conditions similar to those already specified above.

(a) Using oct-1-ene (3 mL) and toluene (4 mL) with CO (380 psig) and $H_2$ (760 psig) with heating to 70° C. for 16 hours, conversion $C_9$ aldehydes was 100% with 69.5% n-nonaldehyde (2.31:1 n-iso)

(b) Using oct-1-ene (3 mL) and toluene (4 mL) with CO (200 psig) and $H_2$ (250 psig) with heating to 70° C. for 14.5 hours conversion to $C_9$ aldehydes was 98.6% with 68.3% n-nonaldehyde. (2.13:1 n:iso) (approx. 1 turnover/min.)

At the end of the examples the solution was clear orange in colour.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What we claim is:

1. A hydroformylation process for the conversion of an olefinic compound having up to 20 carbon atoms to its corresponding aldehyde which process comprises: reacting said olefinic compound in the liquid phase with carbon monoxide and hydrogen at a temperature between 60° and 200° C. and at a pressure of up to 1000 psi or more in the presence of a catalyst comprising a chelate in which a ligand is chelated at a metal center to produce at least one heterocyclic ring with the central metal atom as part of said ring, said catalyst being selected from the group consisting of (A) a platinum group metal complex of bis(phosphinoalkyl)silane having the following Formula I:

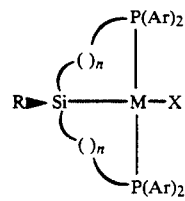

Formula I wherein:

Ar is alkyl, phenyl or modified aryl, cyclohexyl or $C_6H_4X$;

X is Cl, Br, F, $CO_2Me$ or $CO_2CF_3$, or $SnCl_3$;

R is Me, Et, n-Br, T-Bu or cyclohexyl or phenyl;

M is an operative metal selected from the group consisting of Pt, Pd, Rh, and Ir; and $(\ )_n$ is 2, 3, or 4, thereby to provide 2, 3 or 4 C atoms respectively between Si and P:

(B) a platinum-group metal complex having the Formula II

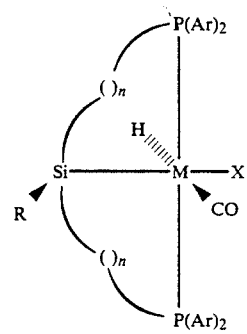

Formula II wherein Ar, X, R, M and $(\ )_n$ are as defined above;

(C) a platinum-group metal complex having the Formula III

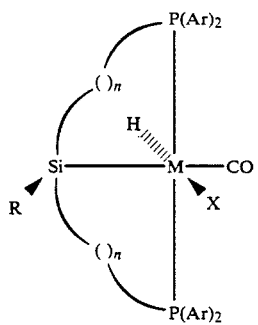

Formula III wherein Ar, X, R, M and $(\ )_n$ are as defined above;

(D) a platinum-group metal complex having the Formula IV

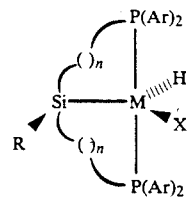

Formula IV wherein Ar, X, R, M and $(\ )_n$ are as defined above;

(E) a platinum-group metal complex of the Formula V

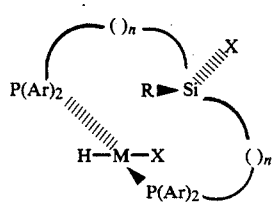

Formula V wherein Ar, X, R, M and ( )$_n$ are as defined above;
(F) a platinum-group metal complex of the Formula VI

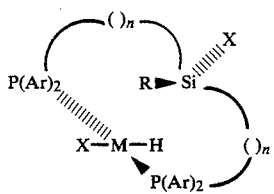

Formula VI wherein Ar, X, R, M and ( )$_n$ are as defined above;
(G) a platinum-group metal complex of tris(phosphinoalkyl) silane having the following Formula VII

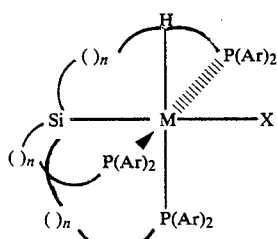

Formula VII wherein Ar, X, M and ( )$_n$ are as defined above;
(H) a platinum-group metal complex having the Formula VIII

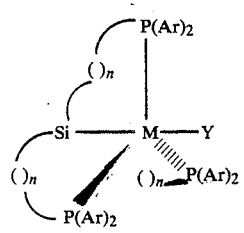

Formula VIII wherein Ar, M and ( )$_n$ are as defined above, and Y=CO, P(Ar)$_3$, or a similar neutral ligand molecule;
(I) a platinum-group metal complex of the Formula IX

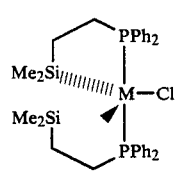

Formula IX (J) a platinum-group metal complex of the Formula X

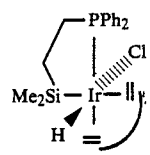

Formula X (K) a platinum-group metal complex of the Formula XI

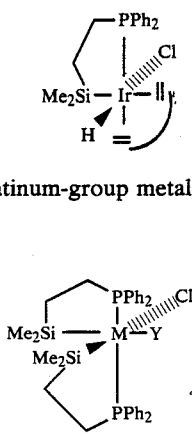

Formula XI (L) a platinum-group metal complex of the Formula XII

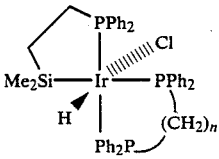

Formula XII (M) a platinum-group metal complex of the Formula XIII

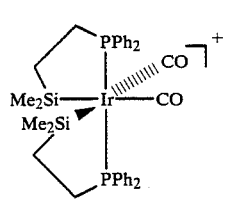

Formula XIII and
(N) a platinum-group metal complex of the Formula XIV

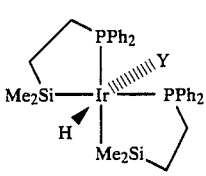

Formula XIV

2. The process of claim 1 wherein said catalyst is a [(phosphinoethyl)silyl]iridium(III) complex.

3. The process of claim 2 wherein said [(phosphinoethyl)silyl]iridium(III) complex is selected from the group consisting of Ir(PPh$_2$CH$_2$CH$_2$SiMe$_2$)(PPh$_3$)(H)(CO)(Cl);

Ir(PPh$_2$CH$_2$CH$_2$SiMe$_2$)(PPh$_3$)($^2$H)(CO)(Cl);

-continued

Ir(PPh₂CH₂CH₂SiPh₂)(PPh₃)(H)(CO)(Cl);

Ir(PPh₂CH₂CH₂SiPh₂)(PPh₃)(²H)(CO)(Cl);

Ir(PPh₂CH₂CH₂SiMePh)(PPh₃)(H)(CO)(Cl);

Ir(PPh₂CH₂CH₂SiMePh)(PPh₃)(²H)(CO)(Cl);

Ir(PPh₂CH₂CH₂SiMeH)(PPh₃)(H)(CO)(Cl);

Ir(PPh₂CH₂CH₂SiMe²H)(PPh₃)(²H)(CO)(Cl);

Ir—(PPh₂CH₂CH₂SiPhH)(PPh₃)(H)(CO)(Cl);

Ir(PPh₂CH₂CH₂SiMe₂)(PPh₃)(H)₂(CO);

Ir(PPh₂CH₂CH₂SiMe₂)₂(H)(CO);

Ir(PPh₂CH₂CH₂SiMe₂)(PPh₃)(H)(CO)(Br); and

Ir(PPh₂CH₂CH₂SiMe₂)(PPh₃)(H)(CO)(I).

4. The process of claim 1 wherein said catalyst is a five-coordinate compound of a phosphinoethylsilyl complex.

5. The process of claim 4 wherein said five-coordinate compound of a phosphinoethylsilyl complex is selected from the group consisting of

[Rh(PPh₂CH₂CH₂SiMe₂)₂Cl];

Ir(PPh₂CH₂CH₂SiMe₂)₂Cl;

[Rh(PPh₂CH₂CH₂SiMe₂)₂Br];

[Rh(PPh₂CH₂CH₂SiMe₂)₂I];

[Ir(PPh₂CH₂CH₂SiMe₂)₂Br]; and

[Ir(PPh₂CH₂CH₂SiMe₂)I].

6. The process of claim 1 wherein said catalyst is a 6-coordinate compound of a phosphinoethylsilyl complex.

7. The process of claim 6 wherein said 6-coordinate compound of a phosphinoethylsilyl complex is selected from the group consisting of

[Ir(PPh₂CH₂CH₂SiMe₂)(COD)(H)(Cl)];

(where COD = cycloocta-1,5-diene)

[Ir(PPh₂CH₂CH₂SiMe₂)(Ph₂PCH₂CH₂PPh₂)(H)(Cl)]; and

[Ir(PPh₂CH₂CH₂SiMe₂)(PPh₂CH₂PPh₂)(H)(Cl)].

8. The process of claim 1 wherein said catalyst is a six-coordinate adduct of two five-coordinate compounds of a phosphinoethylsilyl complex.

9. The process of claim 8 wherein said six-coordinate adduct of two five-coordinate compounds of a phosphinoethylsilyl complex is selected from the group consisting of:

[Rh(PPh₂CH₂CH₂SiMe₂)₂(Cl)(CNBuⁿ)];

[Rh(PPh₂CH₂CH₂SiMe₂)₂(Cl)(CNCMe₃CMe₃)];

[Rh(PPh₂CH₂CH₂SiMe₂)₂(Cl)(CNCHMe₂)];

[Ir(PPh₂CH₂CH₂SiMe₂)₂(Cl)(CO)];

[IrPPh₂CH₂CH₂SiMe₂)₂(Cl)(PF₃)];

[Ir(PPh₂CH₂CH₂SiMe₂)₂(Cl)(P{OMe}₃)];

[Ir(PPh₂CH₂CH₂SiMe₂)₂(Cl)(P{OEt}₃)];

[Ir(PPh₂CH₂CH₂SiMe₂)₂(Cl)(CNBuⁿ)];

[Ir(PPh₂CH₂CH₂SiMe₂)₂(Cl)(CNCMe₂CH₂CMe₃)]; and

[Ir(PPh₂CH₂CH₂SiMe₂)₂(Cl)(CNCHMe₂)].

10. The process of claim 1 wherein said catalyst is a related six-coordinate Ir(III) complex of a five-coordinate compound of a phosphinoethylsilyl complex or a six-coordinate compound of a phosphinoethylsilyl.

11. The process of claim 1 wherein said related six-coordinate IR(III) complex of a five-coordinate compound of a phosphinoethylsilyl complex or a six-coordinate compound of a phosphinoethylsilyl is selected from the group consisting of:

[Ir(PPh₂CH₂CH₂SiMe₂)₂(CO)₂]BF₄;

[Ir(PPh₂CH₂CH₂SiMe₂)₂(H)(CO)]; and

[Ir(PPh₂CH₂CH₂SiMe₂)₂(H)(CNBuᵗ)].

12. The process of claim 1 wherein said catalyst is a chelate-stabilized silyl-iridium (I) complex having the crystal structure

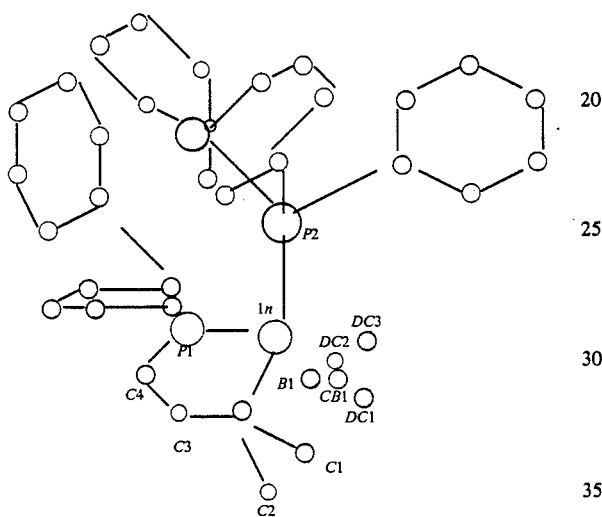

13. The process of claim 1 wherein said catalyst is selected from the group consisting of:

Ir[PPh₂CH₂CH₂Si(Me)CH₂CH₂CH₂PPh₂](H)(Cl);

Rh[PPh₂CH₂CH₂CH₂Si(Me)CH₂CH₂CH₂PPh₂](H)(Cl);

Pt[PPh₂CH₂CH₂CH₂Si(Me)CH₂CH₂CH₂PPh₂]Cl;

Pt[PPh₂CH₂CH₂CH₂Si(Me)CH₂CH₂CH₂PPh₂]SnCl₃;

Pt[PPh₂CH₂CH₂CH₂Si(Me)(Cl)CH₂CH₂CH₂PPh₂](H)Cl;

IrPPh₂CH₂CH₂SiMe(CO)PPh₃H₂;

IrPPh₂CH₂CH₂SiMe₂(C₈H₁₂)H(Cl);

IrPPh₂CH₂CH₂SiMe₂(C₈H₁₂)H(Cl);

IrPPh₂CH₂CH₂SiMe₂PPh₃(CO)H(Cl);

IrPPh₂CH₂CH₂SiMe₂(CO)₂PPh₃;

RhPPh₂(CH₂)₃SiMe(CH₂)₃PPh₂(H)Cl;

Pt[PPh₂CH₂CH₂CH₂Si(Me)CH₂CH₂CH₂PPh₂]Cl + SnCl₂;

Pt[Ph₂PCH₂CH₂Si(Me)₂](PPh₃)(Cl);

Pt[Ph₂PCH₂CH₂Si(Me)₂](Ph₂PMe)(Cl);

Rh[Si(CH₂CH₂PPh₂)₃](H)(Cl);

Rh[Si(CH₂CH₂PPh₂)₃](CO);

Rh[Si(CH₂CH₂PPh₂)₃];

Rh[Si(CH₂CH₂PCy₂)₃](H)(Cl);

Rh[Si(CH₂CH₂PCy₂)₃](CO);

Rh[Si(CH₂CH₂PPh₂)₃](H)(SnCl₃);

Ir[Si(CH₂CH₂PPh₂)₃](H)(Cl);

Ir[Si(CH₂CH₂PPh₂)₃](H)(SnCl₃);

Ir[Si(CH₂CH₂PPh₂)₃](CO);

Ir[Si(CH₂CH₂CH₂PPh₂)₃](H)(Cl);

Ir[Si(CH₂CH₂CH₂PPh₂)₃](CO);

Rh[Si(CH₂CH₂CH₂PPh₂)₃](H)(Cl); and

Rh[Si(CH₂CH₂CH₂PPh₂)₃](CO).

14. The process of claim 1 wherein said olefinic compound is an α-olefin.

15. The process of claim 1 wherein the unsaturated carbon-to-carbon olefinic linkages are between terminal and their adjacent carbon atoms.

16. The process of claim 1 wherein the unsaturated carbon-to-carbon olefinic linkages are between internal chain carbon atoms.

17. The process of claim 1 wherein said olefin is an olefinic hydrocarbon fraction containing $C_7$, $C_8$, $C_9$, $C_{10}$ and higher olefinic fractions as well as olefinic hydrocarbon fractions of wider boiling ranges, selected from $C_{7-9}$, $C_{10-13}$, or $C_{14-17}$ olefinic hydrocarbon fractions.

18. The process of claim 1 wherein said olefin contains 2 to 8 carbon atoms.

19. The process of claim 1 wherein said olefin is an internal olefin having 4–19 carbon atoms.

20. The process of claim 1 wherein said α-olefin is an alkene, an alkyl alkenoate, an alkenyl alkanoate, an alkenyl alkyl ether, or an alkenol, containing up to 20 carbon atoms.

21. The process of claim 1 wherein said olefin is selected from the group consisting of ethylene, propylene, butylene, butene-1, butene-2, pentene-1, benzenes, 2-methylbutene-1, cyclobutene, hexene-1, hexene-2, heptenes, ethyl pentenes, octenes, decenes, nonenes, dodecene, 1-octadecene, dihydronaphthalene, cyclohexene, 3-ethylhexene-1, isobutylene, octene-1, 2-propylhexene-1, ethylcyclohexene, decene-1, cycloheptene, cyclooctene, cyclononene, cyclodecene, cyclododecen, 2-ethyl-1-hexene, styrene, 3-phenyl-1-propene, allyl chloride, 1,4-chloride, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl 7-octenoate, 3-butenoic acid, 7-octenoic acid, 3-butenenitrile, 5-hexenamide, 4,4'-dimethylnonenedodecene-1, undecene-3, 6-propyldecene-1, tetradecene-2, 7-amyldecene-1, oligomers of olefins, e.g. propylene tetramer, ethylene trimer, etc., hexadecene-1, 4-ethyltridecene-1, octadecene-1, 5,5-dipropyldocecene-1, vinylcyclohexane, allylcyclohexane, styrene, p-methylstyrene, alpha-methylstyrene, p-vinylcumene, beta-vinylnaphthanene, 1,1-diphenylethylene, allylbenzene, 6-phenylhexene-1, 1,3-diphenylbutene-1, 3-benzylheptene-1, o-vinyl-p-xylene, divinylbenzene, 1-allyl-4-vinylbenzene, 1,3-butadiene, 1,4-pentadiene, 1,5-hexadiene, 1,4-heptadiene, 1,7-octadiene, 2,6-decadiene, 1,9-dodecadiene, 1,5-hexadiene, 1,4-heptadiene, 1,7-octadiene, 2,6-decadiene, 1,9-dodecadiene, 1,5-hexadecene, 1,4,7-octatriene, 1,4,7,10-undecatetriene, 1,4-cycloheptadiene, 1,5-cyclooctadiene, 1,4,7-cycloderatriene, 1,5,9-cyclododecatriene, 1,5-bicyclo(2,2,2)-heptadiene, 1,2-butadiene, 1,3,5-hexatriene, 2-chloro-1,3-butadiene, 2-chloro-1,3-butadiene, 3,5-monodacadiene, 1,5-hexadiene, 1,5,8-dodecatriene, and 2,6-octadecadiene.

22. The process of claim 1 wherein said temperature is about 70° C. said pressure is about 1000 p.s.i. and wherein the ratio of $CO/H_2$ is about 1:1.

23. The process of claim 1 wherein said olefin is hex-1-ene.

* * * * *